United States Patent
Guda et al.

(10) Patent No.: US 10,465,251 B2
(45) Date of Patent: Nov. 5, 2019

(54) LINCRNA FOR THE DETECTION OF ESOPHAGEAL CANCER

(71) Applicant: CASE WESTERN RESERVE UNIVERSITY, Cleveland, OH (US)

(72) Inventors: Kishore Guda, Cleveland, OH (US); Amitabh Chak, University Heights, OH (US); AnnMarie Kieber-Emmons, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

(21) Appl. No.: 15/568,334

(22) PCT Filed: Apr. 20, 2016

(86) PCT No.: PCT/US2016/028460
§ 371 (c)(1),
(2) Date: Oct. 20, 2017

(87) PCT Pub. No.: WO2016/172225
PCT Pub. Date: Oct. 27, 2016

(65) Prior Publication Data
US 2018/0327849 A1    Nov. 15, 2018

Related U.S. Application Data

(60) Provisional application No. 62/150,128, filed on Apr. 20, 2015.

(51) Int. Cl.
*C12Q 1/6886* (2018.01)
*C12N 15/11* (2006.01)
*C12N 15/113* (2010.01)

(52) U.S. Cl.
CPC .......... *C12Q 1/6886* (2013.01); *C12N 15/111* (2013.01); *C12N 15/113* (2013.01); *C12Q 2600/106* (2013.01); *C12Q 2600/158* (2013.01)

(58) Field of Classification Search
None
See application file for complete search history.

(56) References Cited

U.S. PATENT DOCUMENTS

| | | |
|---|---|---|
| 2012/0004278 A1 | 1/2012 | Chang et al. |
| 2014/0184999 A1 | 7/2014 | Kroll et al. |

FOREIGN PATENT DOCUMENTS

WO    2014/152411 A1    9/2014

OTHER PUBLICATIONS

Leidner et al. "The microRNAs, MiR-31 and MiR-375, as candidate markers in Barrett's esophageal carcinogenesis." Genes Chromosomes Cancer. Feb. 3, 2012 (Feb. 3, 2012), vol. 51, pp. 1-12.
Ulitsky et al. "lincRNAs: genomics, evolution, and mechanisms," Cell, Jul. 3, 2013 (Jul. 3, 2013), vol. 154, pp. 1-35.

*Primary Examiner* — Sean McGarry
(74) *Attorney, Agent, or Firm* — Tarolli, Sundheim, Covell & Tummino LLP

(57) ABSTRACT

A method of analyzing tissue in a subject having or suspected of having cancer includes obtaining an expression profile from a sample of tissue obtained from the subject, wherein the expression profile comprises the level of at least one esophageal adenocarcinoma associated lincRNA selected from the group consisting of linc-PRKD, lincRTL, lincMIA, lincNAV, and lincTMEM.

17 Claims, 3 Drawing Sheets
Specification includes a Sequence Listing.

SEQUENCE LISTING

<160> NUMBER OF SEQ ID NOS: 12

<210> SEQ ID NO 1
<211> LENGTH: 1931
<212> TYPE: DNA
<213> ORGANISM: Homo sapiens

<400> SEQUENCE: 1

```
catgcatttt atttggcaag tctctctcac atctttaatc acactagcct gcccactgcc      60
aatcaataaa gattaggaaa tcgattgcta acttactctt gggttagata ataaaattgt     120
ttgaaacatg cacctggagg aatttatctg tgaagagtcc tttcagagtt tgtttcaagc     180
tttgcaagtc tctcatggct ctgaggtcgg ggaggctgtg agggatcctc cacgcccagc     240
agacgtggaa ggagccgacg ttcttacggg agatggacag acggtcagca tgtgaatagt     300 ccccctgcatg caggtgagga ctgggcagt gcagagccgc agcagggatg ggctatgcct     360
gggagccgcc agctctggat caggtggcca gggacggtca tgctgaagag gaaggctcca     420
gtgaagctct ggaagaatgt tctggtgcag agaggggtg ggtgagctgg ttcccatgga     480
gacaggctca ggatccccag aggccaccag tcctttcttc gtctgacggg agggagggcc     540
ttccgacaag tcacggaact gatcggggga gagctggatg cctgctacac cgtggctctg     600
ctgtctcccg tggaaacccg ggcctctgtt cgagcctgaa gtggcctctc tgcaccaggc     660
tgctgggaga cctgcagtca ccaatggcaa cgtcactctt gcaacagcca gtgggtgtg     720 gggcagcaga cgaagctcga gtaccgcgtt cttccatgtc cagcattctg ctttcagcat     780
cacgggaacg agaggtgatt tccgtaagca ggctccaagg tgccaccacc aagcccagaa     840
gtatctttcc cactttgcag atttcctaca gacccagtat tctctcttcc atgggttgag     900
tttctaaaat cacatgactg tatttttctt ttaatacaga aaagcataat aaaggcataa     960
```

```
aagcccatgc ccctctgcag agcaccctgt tgacattttc tgaaagtaag tcatctatgc    1020
acctgggaag aaagcacaga ggactcagaa aggccaaaaa caaaaacaaa aaagccccac    1080
ctcagcccct gccctctcc cggagaagcc ggagttgtca gcccatgcag cagagttggt    1140
caggagctca agttcacatc ccccaaccgc cacatactac ctgtatcacc tgggcaggtt    1200
ctcccaatac ctcagtgtct tcatctgcaa cgtgggtaag atgggaatgc ccacctcctg    1260
gggaactcag gactcgctga gttaactgca ttcaggacc tgaaagagac tcgccaggca     1320
gtaaccccag tccacttgtt ccatgctggt gtgagcagtg actgcatatt cttccaaaag    1380
catctacccc atctattttt ttttttttt tttgagacag ggtctccctc tgtcacccag     1440
gctggagtgc agtggcatga tctcagctca ctgcaacctc cacctcccgg gttcaagcga    1500
ttctcccgcc tcagcctcct gagtagctgg gattacaggc gtgcaccacc atgcccagct    1560
aatttttgta ttttagtaa agacagggtt tcaccatatt gctcaggctg gtctggaact     1620
cccaacctca ggtgatctgc ccacctcagc ctcccaaggt gctgggatta caggcgtgag    1680
ccaccgcgct gcctatacta tctatttgtt aagccccaaa tggatcatac tttggttcag    1740
cctcttgcgt tctttgcctt gtttatttta gagacctgtc tatctcaatc catgcagata    1800
aatgccttgc tctttcttag gtgccaccaa gcatagacac agacctcccc aatgcccat     1860 ctttcgccat taatcaacag tgttgggatg gtaggacacc aggagttaga cacctcaaag    1920
caccggttct g                                                         1931

<210> SEQ ID NO 2
<211> LENGTH: 383
<212> TYPE: DNA
<213> ORGANISM: Homo sapiens

<400> SEQUENCE: 2
ctcagcccac ctgcacccag gtgaaataaa cagccatgtt gctcacacaa agcctgtttg      60
gtggtctctt cacacagatg tgcatgaaat ttggtgtggt gactcggatc gggggacctg     120
cctcaggaaa tcaatcccct gtcctcctgc tctttgctcc gtgagaaaga tccacctacg     180
acctcaggtc ctcagaccga ctagcccaag aaacatctca ccaatttcaa atctgcactc     240
ccagagcccg tggaactctg gcccaaggct ctctgactga ctccttcttg gcttagcggc     300
tgaagactga cactgcccga tcgcctcaga accccgtag accatcacgg acgccgagct      360
ttagttaact ctcacagtgg agg                                             383

<210> SEQ ID NO 3
<211> LENGTH: 526
<212> TYPE: DNA
<213> ORGANISM: Homo sapiens

<400> SEQUENCE: 3
ctcagcccac ctgcacccag gtgaaataaa cagccatgtt gctcacacaa agcctgtttg      60
gtggtctctt cacacagatg tgcatgaaat ttggtgtggt gactcggatc gggggacctg     120
cctcaggaaa tcaatcccct gtcctcctgc tctttgctcc gtgagaaaga tccacctacg     180
acctcaggtc ctcagaccga ctagcccaag aaacatctca ccaatttcaa atctgcactc     240
ccagagcccg tggaactctg gcccaaggct ctctgactga ctccttcttg gcttagcggc     300
tgaagactga cactgcccga tcgcctcaga accccgtag accatcacgg acgccgagct      360
ttagttaact ctcacagtgg aggcctttgc aagagggtcc gagacatttg catcatcatt     420
```

| cagtgagacc tgtaaacaca gcatctgcct ttgaccacat ccatctggaa gaacctgaga | 480 |
| gataatccat tttatgaaat tttccctacc ctgaaatggg agaatg | 526 |

<210> SEQ ID NO 4
<211> LENGTH: 378
<212> TYPE: DNA
<213> ORGANISM: Homo sapiens

<400> SEQUENCE: 4

| ctcagcccac ctgcacccag gtgaaataaa cagccatgtt gctcacacaa agcctgtttg | 60 |
| gtggtctctt cacacagatg tgcatgaaat ttggtgtggt gactcggatc ggggggacctg | 120 |
| cctcaggaaa tcaatcccct gtcctcctgc tctttgctcc gtgagaaaga tccacctacg | 180 |
| acctcaggtc ctcagaccga ctagcccaag aaacatctca ccaatttcaa atctgccttt | 240 |
| gcaagagggt ccgagacatt tgcatcatca ttcagtgaga cctgtaaaca cagcatctgc | 300 |
| cttttgaccac atccatctgg aagaacctga gagataatcc attttatgaa attttcccta | 360 |
| ccctgaaatg ggagaatg | 378 |

<210> SEQ ID NO 5
<211> LENGTH: 1773
<212> TYPE: DNA
<213> ORGANISM: Homo sapiens

<400> SEQUENCE: 5

| ctcagcccac ctgcacccag gtgaaataaa cagccatgtt gctcacacaa agcctgtttg | 60 |
| gtggtctctt cacacagatg tgcatgaaat ttggtgtggt gactcggatc ggggggacctg | 120 |
| cctcaggaaa tcaatcccct gtcctcctgc tctttgctcc gtgagaaaga tccacctacg | 180 |
| acctcaggtc ctcagaccga ctagcccaag aaacatctca ccaatttcaa atctgcactc | 240 |
| ccagagcccg tggaactctg gcccaaggct ctctgactga ctccttcttg gcttagcggc | 300 |
| tgaagactga cactgcccga tcgcctcaga accccgtag accatcacgg acgccgagct | 360 |
| ttagttaact ctcacagtgg aggcctttgc aagagggtcc gagacatttg catcatcatt | 420 |
| cagtgagacc tgtaaacaca gcatctgcct ttgaccacat ccatctggaa gaacctgaga | 480 |
| gataatccat tttatgaaat tttccctacc ctgaaatggg agaatgatct aatttgaagc | 540 |
| actgagaagg ataaggcatc catttgaaaa ggactcctat attgcaacat gaattctgct | 600 |
| aaaattgaag caagaacaaa catcaaattt atgatgaagt ttgggtagaa gaacgatgaa | 660 |
| attagtgacg ctttataaaa agtttattgg gacaatacccc caaatgaatc agcagtttaa | 720 |
| aaatggataa cttattttaa gaagaaacaa gatgatgttg aagatgaagc ctgcaacggc | 780 |
| agaccatcta catcaatttg gaaggaaaaa attaatcttg ttcatgccct aacggaggaa | 840 |
| gactgacaat taacagcact gacaatagcc aacaatgtag acagctggtt caccttacac | 900 |
| aattctgagt gaaaaattaa aattgagcaa acttttccact caatgagtac caaaactgtt | 960 |
| gtacccaggt tagctgcaaa taacagcaga actttcaatt gaaattttaa acaagtggga | 1020 |
| tcaagatcct gtagcatttc cttgaagaac tgtaacagga gatgaaacat gactttacaa | 1080 |
| tatgatccca aagacataat caaagcataa tcaaagcaat gactgccaag aggtggaaat | 1140 |
| ggtcaagtca cagcaaaagc agatgagcaa tgagcaaagg tcatggcaaa gttttttggt | 1200 |
| gatgttcaag gtgttttact cgttgacttt ctggagggcc aaaaaacaat aacatctact | 1260 |
| aattatgaga gtatttgag aaagtccgtc aaagctttag cagaaaaaca cccaggaaag | 1320 |
| tttcaccaga gagtccttct tcaccatgac aatgttccta ctcattttc tcatcaaaca | 1380 |

| | |
|---|---|
| agggcaattc tgtgagattt tccatgagaa atcattaggc atccacctta cagtcctggt | 1440 |
| ttggttcctt ctaacttctt tttgtttcct aatcttaaga aacttttttac cttaagttaa | 1500 |
| agtatatagc tatttaagat ttcctaatct taaaaaaatt tttcttcagt tgataatatg | 1560 |
| aaaaagattg cactgacata gttaaattcc caagaccctc agttctttat gaatgaacca | 1620 |
| aatggctgat gtcattgttt ataaaagtga cttgaactta acgttctggt aaaccagcac | 1680 |
| cagcctgaag atcacgttct catcaaacgg tggaaagaag aaaaactcga gccaacctag | 1740 |
| gaaggacccc accttgtgct gctaaccacc aag | 1773 |

<210> SEQ ID NO 6
<211> LENGTH: 450
<212> TYPE: DNA
<213> ORGANISM: Homo sapiens

<400> SEQUENCE: 6

| | |
|---|---|
| ctgaatcttc cataagtact ttagaattca gagaaagaag gaatctatga gcccgaatct | 60 |
| ccagggaagg cctcgaggag tggtcatggt ttaaccttag ttccagcttc ggaaatgagg | 120 |
| aggtagggaa agaagcagca aaaattctca gccagacttt gaacaggaag ctttagtaag | 180 |
| agacgtgaat atcttttaaa aataaaagaa ggttgacaca gagatccagg agccaagatg | 240 |
| gccgaatagg aacagctccg gtctacagct cccagcgtga gccacgcaga agacgggtga | 300 |
| tttctgcatt tccatctgag gtaccgggtt catctcacta gggagtgcca cacagtgggc | 360 |
| gcaggtcagt gggtgcgtgc accgtgcgcg agccgaagca gggcgaggca ttgcctcact | 420 |
| ccggaagcgc aaggggtcag ggagttccct | 450 |

<210> SEQ ID NO 7
<211> LENGTH: 560
<212> TYPE: DNA
<213> ORGANISM: Homo sapiens

<400> SEQUENCE: 7

| | |
|---|---|
| aggtgtttcc agaagaggtg agcaattgaa tcagcaaact aaacaaagat tgtcctcatc | 60 |
| aatgtaggtg agcatcagct aacccaggaa gggctttaat ctctgctgtg ccagtttct | 120 |
| atttcagcct tataattttc tgcatttcct tcctctattg cttttcatcc acactttatt | 180 |
| taggaaatgt tcaacagaga agccagaaag gtacctcttc ggaaatgagg aggtagggaa | 240 |
| agaagcagca aaaattctca gccagacttt gaacaggaag ctttagtaag agacgtgaat | 300 |
| atcttttaaa aataaaagaa ggttgacaca gagatccagg agccaagatg gccgaatagg | 360 |
| aacagctccg gtctacagct cccagcgtga gccacgcaga agacgggtga tttctgcatt | 420 |
| tccatctgag gtaccgggtt catctcacta gggagtgcca cacagtgggc gcaggtcagt | 480 |
| gggtgcgtgc accgtgcgcg agccgaagca gggcgaggca ttgcctcact ccggaagcgc | 540 |
| aaggggtcag ggagttccct | 560 |

<210> SEQ ID NO 8
<211> LENGTH: 301
<212> TYPE: DNA
<213> ORGANISM: Homo sapiens

<400> SEQUENCE: 8

| | |
|---|---|
| aggtgtttcc agaagaggtg agcaattgaa tcagcaaact aaacaaagat tgtcctcatc | 60 |
| aatgtaggtg agcatcagct aacccaggaa gggctttaat ctctgctgtg ccagtttct | 120 |

```
atttcagcct tataattttc tgcatttcct tcctctattg cttttcatcc acactttatt        180
taggaaatgt tcaacagaga agccagaaag gtacctcttc ggaaatgagg aggtagggaa        240
agaagcagca aaaattctca gccagacttt gaacaggaag ctttagtaag agaccctgta        300
a                                                                       301
```

<210> SEQ ID NO 9
<211> LENGTH: 105
<212> TYPE: DNA
<213> ORGANISM: Homo sapiens

<400> SEQUENCE: 9

```
ctgaatcttc cataagtact ttagaattca gagaagaag gaatctatga gcccgaatct         60
ccagggaagg cctcgaggag tggtcatggt ttaaccttag ttttg                       105
```

<210> SEQ ID NO 10
<211> LENGTH: 348
<212> TYPE: DNA
<213> ORGANISM: Homo sapiens

<400> SEQUENCE: 10

```
ccagcttcgg aaatgaggag gtagggaaag aagcagcaaa aattctcagc cagactttga         60
acaggaagct ttagtaagag acgtgaatat cttttaaaaa taaagaagg ttgacacaga        120 gatccaggag ccaagatggc cgaataggaa cagctccggt ctacagctcc agcgtgagc        180 cacgcagaag acgggtgatt tctgcatttc catctgaggt accgggttca tctcactagg        240
gagtgccaca cagtgggcgc aggtcagtgg gtgcgtgcac cgtgcgcgag ccgaagcagg        300
gcgaggcatt gcctcactcc ggaagcgcaa ggggtcaggg agttccct                    348
```

<210> SEQ ID NO 11
<211> LENGTH: 771
<212> TYPE: DNA
<213> ORGANISM: Homo sapiens

<400> SEQUENCE: 11

```
ccaggcagtc acctagctgc tgttatgctg catacctgtc tctgagtact cgcttcatcc         60
atcggccagg gtctgtggga cagaccaggc aggtggtgcc ccatgtgagg aacgctgcaa        120
tggattgcaa gggaacccct gaaaacaaat gtgaagtgac tgagcatgtt aaccttagaa        180
gactagaacc taatgagtta tggcaaacag atgttatgca cgtccctgaa tttggaaaac        240
taagacgagg catcaaacca taccatggca tggctaggac ccaacccggt accaaaatga        300
agaaaatgac cctacaggac ccacaatccc ggatgatgtg gcttccttgg atgacacagg        360
ccctggacat tacctggggg atgctgaaga agacaactca ggaggccaag caaatcctgc        420
tccaggcaca gacaccattc actccagaag ctgccattca ttcgacataa gtaggtgctt        480
catctgataa gcgctgcttg tgtaatttat caatgacaga gaaggcagat agcagcatgc        540
atacttgggg ctgcatttga aggagagcaa catcccttg ttttcacaga gagaacaagc        600
atgagttgag attgtggtgc ttcttgaagt ctcatccaga tcagaaacct gctgctctgt        660
ccacattcca tccaccaaag caacccatat ggccatgtcc agcatcagat ggggaaaggc        720
agttctcctc tagcacgagg agctgcaaag ccacatggca aaggatgagt g                771
```

<210> SEQ ID NO 12
<211> LENGTH: 567
<212> TYPE: DNA
<213> ORGANISM: Homo sapiens

<400> SEQUENCE: 12

```
ccaggcagtc acctagctgc tgttatgctg catacctgtc tctgagtact cgcttcatcc        60
atcggccagg gtctgtggga cagaccaggc aggtggtgcc ccatgtgagg aacgctgcaa       120
tggattgcaa gggaacccct gaaaacaaat gtgaagtgac tgagcatgtt aaccttagaa       180
gactagaacc taatgagtta tggcaaacag atgttatgca cgtccctgaa tttggaaaac       240
taaggtcctc tttggattcc agcacgaggc atcaaaccat accatggcat ggctaggacc       300
caacccggta ccaaaatgaa gaaaatgacc ctacaggacc cacaatcccg gatgatgtgg       360
cttccttgga tgacacaggc cctggacatt acctggggga tgctgaagaa gacaactcag       420
gaggccaagc aaatcctgct ccaggcacag acaccattca ctccagaact ccagaagaga       480
agggcctttt tccactgtgt ccattgatga atcttcatca ctgagaatgg aatatgccac       540
atagcagatg ctcaataaat atgttga                                           567
```

LINCRNA FOR THE DETECTION OF ESOPHAGEAL CANCER

RELATED APPLICATION

This application claims priority from U.S. Provisional Application No. 62/150,128, filed Apr. 20, 2015, the subject matter of which is incorporated herein by reference in its entirety.

GOVERNMENT FUNDING

This invention was made with government support under Grant No. CA148980, CA163060, CA150964, awarded by The National Cancer Institute and DK083251 awarded by The National Institute of Diabetes and Digestive and Kidney Diseases. The United States government has certain rights to the invention.

BACKGROUND

Prospectively collected Surveillance Epidemiology and End Results (SEER) data indicate that the incidence of esophageal adenocarcinoma (EAC) has increased more than 5-fold in the past three decades. Over 10,000 cases are now diagnosed annually. The prognosis for patients with EAC is poor with less than 20% of patients surviving beyond 5 years.

Barrett's esophagus (BE), a pre-malignant metaplastic condition that is the only known precursor of EAC, is diagnosed when patients undergo upper endoscopy (EGD) often for symptoms of gastroesophageal reflux disease (GERD). Once BE has been diagnosed, subsequent surveillance with periodic EGD is the current strategy for the early detection of dysplasia/cancer. However, most patients with BE do not progress to EAC and surveillance may or may not result in improved survival. Thus, it is imperative to develop surveillance strategies that target only the selected few with the greatest risk of progression to dysplasia and cancer and stop surveying those with no risk of progression.

Endoscopic surveillance strategies are based on the identification of dysplasia in random biopsies. Poor agreement among pathologists in interpreting dysplasia and the reliance of this strategy on random endoscopic biopsies, which sample only a small fraction of the BE segment are two major factors that explain why surveillance is ineffective. Robust molecular markers that predict the progression of BE to EAC would improve the efficacy of surveillance by enabling a more robust diagnosis of dysplasia, especially if the markers were applied to endoscopic brushings obtained from the entire segment of BE.

Patients with BE who are diagnosed with high grade dysplasia or low grade dysplasia can be treated with endoscopic ablation. Ablative therapies can prevent the progression of BE to cancer. However, some patients who undergo ablation may still develop cancer. Therefore, these patients need to be followed closely. Molecular markers that can identify dysplasia and risk of progression to cancer would guide ablative therapies and would be useful in following these patients after ablation.

The final challenge lies in patients who develop EAC. The prognosis of these patients is poor because the majority of them develop invasive metastatic cancer. These patients are often treated with concurrent chemotherapy and radiation therapy. Cis-platin plus 5-FU combination chemotherapy, the most commonly used regimen, has a response rate of less than 50% in EAC patients. Other regimens based around taxanes or irinotecan also have similar response rates. Molecular markers that can guide the selection of chemotherapy or radiation therapy regimens and predict which cancers will respond would improve the treatment of EAC patients. Moreover, development of new evidence-based therapeutic targets would significantly aid in the treatment of advanced EACs, and in preventing disease recurrence or metastatic spread, and in the overall management of the disease.

SUMMARY

Embodiments described herein relate to RNAs (e.g., lincRNAs) associated with increased risk of esophageal neoplasias that include Barrett's esophagus with high grade dysplasia, or esophageal or gastric cancers (e.g., esophageal adenocarcinoma), methods and compositions of modulating the levels of lincRNAs in cells associated with high grade dysplasia or esophageal cancers (e.g., esophageal cells or esophageal cancer cells) of the subject to treat or prevent gastric or esophageal cancers, and/or methods of measuring the expression profile of esophageal adenocarcinoma lincRNAs to monitor the progression of Barrett's esophagus to high grade dysplasia or esophageal adenocarcinoma and/or to determine whether the subject has high grade dysplasia or esophageal adenocarcinoma or an increased risk of high grade dysplasia or esophageal adenocarcinoma and/or the efficacy of a therapeutic regimen or agent.

In some embodiments, cancer in a subject can be treated by administering an agent to cancer cells of the subject that is effective to modulate the level of esophageal adenocarcinoma associated lincRNA in the esophageal cells or esophageal cancer cells.

In some embodiments, the agent administered to the cancer cells to treat cancer in the subject can be effective to decrease the level of esophageal adenocarcinoma associated lincRNA, which is over expressed in the cancer cells compared to normal cells. An agent effective to decrease the level of esophageal adenocarcinoma associated lincRNA, which is over expressed in the cancer cells, can include an RNA inhibitor of the esophageal adenocarcinoma associated lincRNA, such as siRNA, miRNA, stRNA, snRNA, shRNA, and antisense nucleic acids to the esophageal adenocarcinoma associated lincRNA.

In one example, the esophageal adenocarcinoma associated lincRNA that is over expressed or upregulated, can include at least one of lincPRKD, lincRTL, lincMIA, or lincNAV.

In other embodiments, the agent administered to the esophageal cancer cells to treat esophageal cancer in the subject can be effective to increase the level of esophageal adenocarcinoma associated lincRNA that is under expressed or downregulated in the esophageal cancer cells compared to normal cells. The agent can include, for example, a nucleic acid encoding the under expressed esophageal adenocarcinoma associated lincRNA that is administered to the cancer cells using, for example, an expression vector.

In one example, the esophageal adenocarcinoma associated lincRNA that is under expressed or down regulated in the esophageal cancer cells can include lincTMEM.

Other embodiments described herein relate to a method of analyzing bodily sample, such as bodily cells or tissue (e.g., gastric biopsy cell, or tissue) from a subject having or suspected of having Barrett's esophagus with high grade dysplasia and/or esophageal adenocarcinoma. The method includes obtaining an expression profile from a sample obtained from the subject, wherein the expression profile comprises the level of at least one esophageal adenocarcinoma associated lincRNA selected from the group consisting of lincPRKD, lincRTL, lincMIA, lincNAV, lincTMEM and combinations thereof. The expression profile from the sample is then compared to an expression profile of a control or standard. A decrease in the expression of the esophageal adenocarcinoma associated lincRNA lincTMEM, and and/or an increase in the expression of the at least one esophageal adenocarcinoma associated lincRNA selected from the group consisting of lincPRKD, lincRTL, lincMIA, lincNAV, and combinations thereof is indicative of the subject having high grade dysplasia and/or esophageal adenocarcinoma and/or an increased risk of high grade dysplasia and/or esophageal adenocarcinoma. In some embodiments, the bodily sample is a gastric biopsy sample obtained from a subject having or suspected of having Barrett's esophagus and/or gastric esophageal reflux disease.

Still other embodiments relate to a method of predicting whether a subject has high grade dysplasia and/or esophageal adenocarcinoma or an increased risk of high grade dysplasia and/or esophageal adenocarcinoma. The method includes obtaining an expression profile from a bodily sample obtained from the subject, wherein the expression profile comprises the level of at least one esophageal adenocarcinoma associated lincRNA selected from the group consisting of lincPRKD, lincRTL, lincMIA, lincNAV, lincTMEM and combinations thereof. The expression profile from the sample is then compared to an expression profile of a control or standard and whether the subject has high grade dysplasia and/or esophageal adenocarcinoma or an increased risk of high grade dysplasia and/or esophageal adenocarcinoma is predicted based on (i) deviation of the expression profile of the sample from a control or standard derived from a healthy individual or population of healthy individuals, or (ii) the similarity of expression profiles of the sample and a control or standard derived from an individual or population of individuals who have or have had the cancer. In some embodiments, a decrease in the expression of the esophageal adenocarcinoma associated lincTMEM and and/or an increase in the expression of the at least one esophageal adenocarcinoma associated lincRNA selected from the group consisting of lincPRKD, lincRTL, lincMIA, lincNAV, and combinations thereof is indicative of the subject having high grade dysplasia and/or esophageal adenocarcinoma or an increased risk of high grade dysplasia and/or esophageal adenocarcinoma. In some embodiments, the bodily sample is a gastric biopsy sample obtained from a subject having or suspected of having Barrett's esophagus.

Other embodiments relate to a method of monitoring a subject's response to a treatment regimen for cancer. The method includes administering a therapeutic regimen to the subject. An expression profile from a bodily sample is obtained from the subject, the expression profile comprises the level of at least one esophageal adenocarcinoma associated lincRNA selected from the group consisting of lincPRKD, lincRTL, lincMIA, lincNAV, lincTMEM and combinations thereof. The expression profile from the sample is compared to an expression profile of a control or standard. An increase in the expression of the esophageal adenocarcinoma associated lincTMEM and and/or a decrease in the expression of the at least one esophageal adenocarcinoma associated lincRNA selected from the group consisting of lincPRKD, lincRTL, lincMIA, lincNAV, and combinations thereof is indicative of an increased efficacy of the therapeutic regimen.

DETAILED DESCRIPTION

Figure 1:
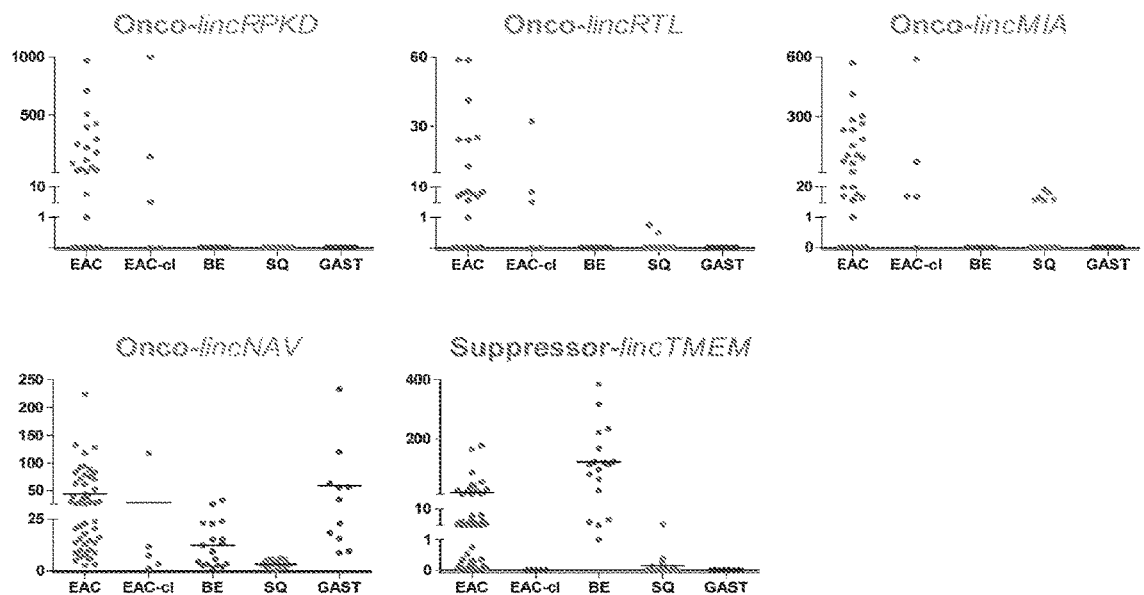
FIG. 1 illustrates plots showing novel lincRNAs associated with EAC progression.

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

It is to be understood that this invention is not limited to the particular methodology, protocols, cell lines, plant species or genera, constructs, and reagents described as such. It is also to be understood that the terminology used herein is for the purpose of describing particular embodiments only, and is not intended to limit the scope of the present invention which will be limited only by the appended claims.

The term "pharmaceutically acceptable carrier" refers to any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

The term "subject" refers to any organism or animal to whom treatment or prophylaxis treatment is desired. Such animals include mammals, preferably a human.

The term "mammal" or "mammalian" are used interchangeably herein, and encompass their normal meaning. While the methods and compositions described herein are most desirably intended for efficacy in humans, they may also be employed in domestic mammals such as canines, felines, and equines, as well as in mammals of particular interest, e.g., zoo animals, farmstock, transgenic animals, rodents and the like.

The terms "gene silencing" or "gene silenced" in reference to an activity of a RNAi molecule, for example a siRNA or miRNA refers to a decrease in the mRNA level in a cell for a heterologous target gene by at least about 5%, about 10%, about 20%, about 30%, about 40%, about 50%, about 60%, about 70%, about 80%, about 90%, about 95%, about 99%, about 100% of the mRNA level found in the cell without the presence of the miRNA or RNA interference molecule. In one embodiment, the mRNA levels are decreased by at least about 70%, about 80%, about 90%, about 95%, about 99%, about 100%. As used herein, the "reduced" or "gene silencing" refers to lower, preferably significantly lower, more preferably the expression of the nucleotide sequence is not detectable.

The term "double-stranded RNA" molecule, "RNAi molecule", or "dsRNA" molecule refers to a sense RNA fragment of a nucleotide sequence and an antisense RNA fragment of the nucleotide sequence, which both comprise nucleotide sequences complementary to one another, thereby allowing the sense and antisense RNA fragments to pair and form a double-stranded RNA molecule. In some embodiments, the terms refer to a double-stranded RNA molecule capable, when expressed, is at least partially reducing the level of the mRNA of the heterologous target gene. In particular, the RNAi molecule is complementary to a synthetic RNAi target sequence located in a non-coding region of the heterologous target gene.

The terms "RNA interference", "RNAi", and "dsRNAi" are used interchangeably herein and refer to nucleic acid molecules capable of gene silencing.

The term "RNAi" refers to any type of interfering RNA, including siRNAi, shRNAi, stRNAi, endogenous microRNA and artificial microRNA. For instance, it includes sequences previously identified as siRNA, regardless of the mechanism of down-stream processing of the RNA. The term "siRNA" also refers to a nucleic acid that forms a double stranded RNA, which double stranded RNA has the ability to reduce or inhibit expression of a gene or target gene when the siRNA is present or expressed in the same cell as the target gene. The double stranded RNA siRNA can be formed by the complementary strands. In one embodiment, a siRNA refers to a nucleic acid that can form a double stranded siRNA. The sequence of the siRNA can correspond to the full length target gene, or a subsequence thereof. Typically, the siRNA is at least about 10-50 nucleotides in length (e.g., each complementary sequence of the double stranded siRNA is about 10-22 nucleotides in length, and the double stranded siRNA is about 10-22 base pairs in length, preferably about 19-22 base nucleotides, preferably about 17-19 nucleotides in length, e.g., 10, 11, 12, 13, 14, 15, 16, 17, 18, 19, 20, 21, or 22 nucleotides in length).

The terms "shRNA" or "small hairpin RNA" (also called stem loop) is a type of siRNA. In one embodiment, these shRNAs are composed of a short, e.g., about 10 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

The term a "stem-loop structure" refers to a nucleic acid having a secondary structure that includes a region of nucleotides, which are known or predicted to form a double strand (stem portion) that is linked on one side by a region of predominantly single-stranded nucleotides (loop portion). The terms "hairpin" and "fold-back" structures are also used herein to refer to stem-loop structures. Such structures are well known in the art and the term is used consistently with its known meaning in the art. The actual primary sequence of nucleotides within the stem-loop structure is not critical to the practice of the invention as long as the secondary structure is present. As is known in the art, the secondary structure does not require exact base-pairing. Thus, the stem may include one or more base mismatches. Alternatively, the base-pairing may be exact, i.e., not include any mismatches. In some instances the precursor microRNA molecule may include more than one stem-loop structure. The multiple stem-loop structures may be linked to one another through a linker, such as, for example, a nucleic acid linker or by a microRNA flanking sequence or other molecule or some combination thereof. The actual primary sequence of nucleotides within the stem-loop structure is not critical as long as the secondary structure is present. As is known in the art, the secondary structure does not require exact base-pairing. Thus, the stem may include one or more base mismatches. Alternatively, the base pairing may not include any mismatches.

The term "hairpin RNA" refers to any self-annealing double stranded RNA molecule. In its simplest representation, a hairpin RNA consists of a double stranded stem made up by the annealing RNA strands, connected by a single stranded RNA loop, and is also referred to as a "pan-handle RNA". However, the term "hairpin RNA" is also intended to encompass more complicated secondary RNA structures comprising self-annealing double stranded RNA sequences, but also internal bulges and loops. The specific secondary structure adapted will be determined by the free energy of the RNA molecule, and can be predicted for different situations using appropriate software such as FOLDRNA (Zuker and Stiegler (1981) Nucleic Acids Res 9(1):133-48; Zuker, M. (1989) Methods Enzymol. 180, 262-288).

The term "agent" refers to any entity, which is normally absent or not present at the levels being administered, in the cell. An agent may be selected from a group comprising; chemicals; small molecules; nucleic acid sequences; nucleic acid analogues; proteins; peptides; aptamers; antibodies; or fragments thereof. A nucleic acid sequence may be RNA or DNA, and may be single or double stranded, and can be selected from a group comprising; nucleic acid encoding a protein of interest, oligonucleotides, nucleic acid analogues, for example peptide-nucleic acid (PNA), pseudo-complementary PNA (pc-PNA), locked nucleic acid (LNA), etc. Such nucleic acid sequences include, for example, but not limited to, nucleic acid sequence encoding proteins, for example that act as transcriptional repressors, antisense molecules, ribozymes, small inhibitory nucleic acid sequences, for example but not limited to RNAi, shRNAi, siRNA, micro RNAi (mRNAi), antisense oligonucleotides etc. A protein and/or peptide or fragment thereof can be any protein of interest, for example, but not limited to; mutated proteins; therapeutic proteins; truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, tribodies, humanized proteins, humanized antibodies, chimeric antibodies, modified proteins and fragments thereof. The agent may be applied to the media, where it contacts the cell and induces its effects. Alternatively, the agent may be intracellular within the cell as a result of introduction of the nucleic acid sequence into the cell and its transcription resulting in the production of the nucleic acid and/or protein environmental stimuli within the cell. In some embodiments, the agent is any chemical, entity or moiety, including without limitation synthetic and naturally-occurring non-proteinaceous entities. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Agents can be known to have a desired activity and/or property, or can be selected from a library of diverse compounds.

The terms "a reduction" of the level of an RNA, mRNA, rRNA, tRNA, or lincRNA includes a decrease in the level of the RNA, mRNA, rRNA, tRNA, or lincRNA in the cell or organism. "At least a partial reduction" of the level of the RNA, mRNA, rRNA, tRNA or lincRNA means that the level is reduced at least about 10%, at least about 25%, at least 50% or more relative to a cell or organism in which the level of RNA, mRNA, rRNA, tRNA or lincRNA is not reduced by some means. "A substantial reduction" of the level of RNA, mRNA, rRNA, tRNA or lincRNA means that the level is reduced at least about 75%, at least about 85% or more. The reduction can be determined by methods with which the skilled worker is familiar Thus, the reduction can be determined for example by reverse transcription (quantitative RT-PCR), ELISA (enzyme-linked immunosorbent assay), Western blotting, radioimmunoassay (RIA) or other immunoassays and fluorescence-activated cell analysis (FACS).

In its broadest sense, the term "substantially complementary", when used herein with respect to a nucleotide sequence in relation to a reference or target nucleotide sequence, means a nucleotide sequence having a percentage of identity between the substantially complementary nucleotide sequence and the exact complementary sequence of said reference or target nucleotide sequence of at least 60%, at least 70%, at least 80% or 85%, at least 90%, at least 93%, at least 95% or 96%, at least 97% or 98%, at least 99% or 100% (the later being equivalent to the term "identical" in this context). For example, identity is assessed over a length of at least 10 nucleotides, or at least 11, 12, 13, 14, 15, 16, 17, 18, 19, 20, 21, 22 or up to 50 nucleotides of the entire length of the nucleic acid sequence to said reference sequence (if not specified otherwise below). Sequence comparisons are carried out using default GAP analysis with the University of Wisconsin GCG, SEQWEB application of GAP, based on the algorithm of Needleman and Wunsch (Needleman and Wunsch (1970) J Mol. Biol. 48: 443-453; as defined above). A nucleotide sequence "substantially complementary" to a reference nucleotide sequence hybridizes to the reference nucleotide sequence under low stringency conditions, preferably medium stringency conditions, most preferably, high stringency conditions (as defined above).

The term "substantially identical", when used herein with respect to a nucleotide sequence, means a nucleotide sequence corresponding to a reference or target nucleotide sequence, wherein the percentage of identity between the substantially identical nucleotide sequence and the reference or target nucleotide sequence is at least 60%, at least 70%, at least 80% or 85%, at least 90%, at least 93%, at least 95% or 96%, at least 97% or 98%, at least 99% or 100% (the later being equivalent to the term "identical" in this context). For example, identity is assessed over a length of 10-22 nucleotides, such as at least 10, 11, 12, 13, 14, 15, 16, 17, 18, 19, 20, 21, 22 or up to 50 nucleotides of a nucleic acid sequence to said reference sequence (if not specified otherwise below). Sequence comparisons are carried out using default GAP analysis with the University of Wisconsin GCG, SEQWEB application of GAP, based on the algorithm of Needleman and Wunsch (Needleman and Wunsch (1970) J Mol. Biol. 48: 443-453; as defined above). A nucleotide sequence "substantially identical" to a reference nucleotide sequence hybridizes to the exact complementary sequence of the reference nucleotide sequence (i.e., its corresponding strand in a double-stranded molecule) under low stringency conditions, preferably medium stringency conditions, most preferably high stringency conditions (as defined above). Homologues of a specific nucleotide sequence include nucleotide sequences that encode an amino acid sequence that is at least 24% identical, at least 35% identical, at least 50% identical, at least 65% identical to the reference amino acid sequence, as measured using the parameters described above, wherein the amino acid sequence encoded by the homolog has the same biological activity as the protein encoded by the specific nucleotide. The term "substantially non-identical" refers to a nucleotide sequence that does not hybridize to the nucleic acid sequence under stringent conditions.

The term "disease" or "disorder" is used interchangeably herein, refers to any alternation in state of the body or of some of the organs, interrupting or disturbing the performance of the functions and/or causing symptoms such as discomfort, dysfunction, distress, or even death to the person afflicted or those in contact with a person. A disease or disorder can also related to a distemper, ailing, ailment, malady, disorder, sickness, illness, complaint, inderdisposion, affection.

The terms "malignancy" or "cancer" are used interchangeably herein and refers to any disease of an organ or tissue in mammals characterized by poorly controlled or uncontrolled multiplication of normal or abnormal cells in that tissue and its effect on the body as a whole. Cancer diseases within the scope of the definition comprise benign neoplasms, dysplasias, hyperplasias as well as neoplasms showing metastatic growth or any other transformations like e.g., leukoplakias which often precede a breakout of cancer. The term "tumor" or "tumor cell" are used interchangeably herein, refers to the tissue mass or tissue type of cell that is undergoing abnormal proliferation.

The term "biological sample" or "sample" as used herein refers to a cell or population of cells or a quantity of tissue or fluid from a subject. Most often, the sample has been removed from a subject, but the term "biological sample" can also refer to cells or tissue analyzed in vivo, i.e., without removal from the subject. Often, a "biological sample" will contain cells from the animal, but the term can also refer to non-cellular biological material, such as non-cellular fractions of blood, saliva, or urine, that can be used to measure gene or protein expression levels. Biological samples include, but are not limited to, tissue biopsies, scrapes (e.g., buccal scrapes), whole blood, plasma, serum, urine, saliva, cell culture, or cerebrospinal fluid. Biological samples also include tissue biopsies, cell culture. A biological sample or tissue sample can refers to a sample of tissue or fluid isolated from an individual, including but not limited to, for example, blood, plasma, serum, tumor biopsy, urine, stool, sputum, spinal fluid, pleural fluid, nipple aspirates, lymph fluid, the external sections of the skin, respiratory, intestinal, and genitourinary tracts, tears, saliva, milk, cells (including but not limited to blood cells), tumors, organs, and also samples of in vitro cell culture constituent. In some embodiments, the sample is from a resection, biopsy, or core needle biopsy of a primary or metastatic tumor, or a cellblock from pleural fluid. In addition, fine needle aspirate samples are used. Samples may be either paraffin-embedded or frozen tissue. The sample can be obtained by removing a sample of cells from a subject, but can also be accomplished by using previously isolated cells (e.g., isolated by another person), or by performing the methods of the invention in vivo. Biological sample also refers to a sample of tissue or fluid isolated from an individual, including but not limited to, for example, blood, plasma, serum, tumor biopsy, urine, stool, sputum, spinal fluid, pleural fluid, nipple aspirates, lymph fluid, the external sections of the skin, respiratory, intestinal, and genitourinary tracts, tears, saliva, milk, cells (including but not limited to blood cells), tumors, organs, and also samples of in vitro cell culture constituent. In some embodiments, the biological samples can be prepared, for example biological samples may be fresh, fixed, frozen, or embedded in paraffin.

The term "tissue" is intended to include intact cells, blood, blood preparations such as plasma and serum, bones, joints, muscles, smooth muscles, and organs.

The term "treatment" refers to any treatment of a pathologic condition in a subject, particularly a human subject, and includes one or more of the following: (a) preventing a pathological condition from occurring in a subject which may be predisposition to the condition but has not yet been diagnosed with the condition and, accordingly, the treatment constitutes prophylactic treatment for the disease or condition; (b) inhibiting the pathological condition, i.e., arresting its development, (c) relieving the pathological condition, i.e. causing a regression of the pathological condition; or (d) relieving the conditions mediated by the pathological condition.

The term "computer" refers to any non-human apparatus that is capable of accepting a structured input, processing the structured input according to prescribed rules, and producing results of the processing as output. Examples of a computer include: a computer; a general purpose computer; a supercomputer; a mainframe; a super mini-computer; a mini-computer; a workstation; a micro-computer; a server; an interactive television; a hybrid combination of a computer and an interactive television; and application-specific hardware to emulate a computer and/or software. A computer can have a single processor or multiple processors, which can operate in parallel and/or not in parallel. A computer also refers to two or more computers connected together via a network for transmitting or receiving information between the computers. An example of such a computer includes a distributed computer system for processing information via computers linked by a network.

The term "computer-readable medium" may refer to any storage device used for storing data accessible by a computer, as well as any other means for providing access to data by a computer. Examples of a storage-device-type computer-readable medium include: a magnetic hard disk; a floppy disk; an optical disk, such as a CD-ROM and a DVD; a magnetic tape; a memory chip.

The term "software" is used interchangeably herein with "program" and refers to prescribed rules to operate a computer. Examples of software include: software; code segments; instructions; computer programs; and programmed logic.

The term a "computer system" may refer to a system having a computer, where the computer comprises a computer-readable medium embodying software to operate the computer.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

The term "optional" or "optionally" means that the subsequent described event, circumstance or substituent may or may not occur, and that the description includes instances where the event or circumstance occurs and instances where it does not.

Other than in the operating examples, or where otherwise indicated, all numbers expressing quantities of ingredients or reaction conditions used herein should be understood as modified in all instances by the term "about." The term "about" when used in connection with percentages can mean +/−0.1%.

As used herein, the word "or" means any one member of a particular list and also includes any combination of members of that list. The words "comprise," "comprising," "include," "including," and "includes" when used in this specification and in the following claims are intended to specify the presence of one or more stated features, integers, components, or steps, but they do not preclude the presence or addition of one or more other features, integers, components, steps, or groups thereof.

In this specification and the appended claims, the singular forms "a," "an," and "the" include plural references unless the context clearly dictates otherwise, and therefore "a" and "an" are used herein to refer to one or to more than one (i.e., at least one) of the grammatical object of the article. By way of example, "an element" means one element or more than one element, and reference to a composition for delivering "an agent" includes reference to one or more agents.

Compositions or methods "comprising" one or more recited elements may include other elements not specifically recited. For example, a composition that comprises an inhibitor of esophageal associated lincRNA encompasses both an inhibitor of esophageal associated lincRNA but may also include other agents or other components. By way of further example, a composition that comprises elements A and B also encompasses a composition consisting of A, B and C. The terms "comprising" means "including principally, but not necessary solely". Furthermore, variation of the word "comprising", such as "comprise" and "comprises", have correspondingly varied meanings. The term "consisting essentially" means "including principally, but not necessary solely at least one", and as such, is intended to mean a "selection of one or more, and in any combination."

Embodiments described herein relate to RNAs (e.g., lincRNAs) associated with increased risk of esophageal neoplasias that include Barrett's esophagus with high grade dysplasia, or esophageal or gastric cancers (e.g., esophageal adenocarcinoma), methods and compositions of modulating the levels of lincRNAs in cells associated with high grade dysplasia or esophageal cancers (e.g., esophageal cells or esophageal cancer cells) of the subject to treat or prevent gastric or esophageal cancers, and/or methods of measuring the expression profile of esophageal adenocarcinoma lincRNAs to monitor the progression of Barrett's esophagus to high grade dysplasia or esophageal adenocarcinoma and/or to determine whether the subject has high grade dysplasia or esophageal adenocarcinoma or an increased risk of high grade dysplasia or esophageal adenocarcinoma and/or the efficacy of a therapeutic regimen agent.

lincRNAs are a special class of evolutionarily conserved non-coding RNAs that are predominantly implicated in regulating gene transcription via interaction with chromatin remodeling complexes. lincRNAs are becoming more attractive as cancer biomarkers due to their newly recognized functional roles as regulatory molecules involved in carcinogenesis. To date, no studies have been performed to characterize the lincRNAs in the Barrett's disease model. We innovatively used RNA sequencing to genome-wide profile the expression of 8000 lincRNAs in 56 pre-treatment esophageal adenocarcinoma biopsies, 18 Barrett's esophagus lesions obtained from patients with no history of dysplasia or cancer development (median surveillance of 9 years, ranging from 6 to 22 years), 20 normal SQ biopsies matching 20 of the esophageal adenocarcinoma cases, and 11 normal gastric (GAST) biopsy samples. Using a stringent selection criteria, we identified five novel lincRNAs, lincPRKD, lincRTL, lincMIA, lincNAV, and lincTMEM, as markedly deregulated in esophageal adenocarcinomas. We further confirmed the differential expression of these lincRNAs using quantitative real-time PCR (qPCR). Together, deregulations in these 5 candidates accounted for >80% of the EAC cases with each lincRNA showing alterations in at least about 30% of esophageal adenocarcinomas. Furthermore, our phenotypic analyses in esophageal adenocarcinoma cell line models using antisense molecules against two of the candidate lincRNAs, lincPRKD and lincRTL, showed marked growth suppression of esophageal adenocarcinoma cells, supporting a role for these lincRNAs in esophageal adenocarcinoma progression.

Some embodiments described herein therefore relate to compositions and methods for analyzing a bodily sample, such as bodily cells or tissue (e.g., gastric biopsy tissue) from a subject having or suspected of having Barrett's esophagus with high grade dysplasia and/or esophageal adenocarcinoma. The method includes measuring the level of at least one esophageal adenocarcinoma associated lincRNA selected from the group consisting of lincPRKD, lincRTL, lincMIA, lincNAV, lincTMEM and combinations thereof. LincRNA transcript sequences in accordance with some embodiments include lincRTL (SEQ ID NO: 1), lincMIA (SEQ ID NO: 2, SEQ ID NO: 3, SEQ ID NO: 4, or SEQ ID NO: 5), lincPRKD (SEQ ID NO: 6, SEQ ID NO:7, SEQ ID NO: 8, SEQ ID NO: 9, SEQ ID NO: 10), lincTMEM (SEQ ID NO: 11 or SEQ ID NO: 12).

The level of the at least one esophageal adenocarcinoma associated lincRNA from the sample is then compared to a control level or standard. A decrease in the expression of the esophageal adenocarcinoma associated lincRNA lincTMEM, and and/or increase in the expression of the at least one esophageal adenocarcinoma associated lincRNA selected from the group consisting of lincPRKD, lincRTL, lincMIA, lincNAV, and combinations thereof is indicative of the subject having high grade dysplasia and/or esophageal adenocarcinoma and/or an increased risk of high grade dysplasia and/or esophageal adenocarcinoma. In some embodiments, the bodily sample is a gastric biopsy sample obtained from a subject having or suspected of having Barrett's esophagus or gastric esophageal reflux disease.

The measuring methods can include any method of nucleic acid detection, for example in situ hybridization for esophageal adenocarcinoma associated lincRNA using antisense DNA or RNA oligonucleotide probes, ultra-high throughput sequencing, Nanostring technology, microarrays, rolling circle amplification, proximity-mediated ligation, PCR, qRT-PCR ChIP, ChIP-qPCR or antibodies, or nucleic acid measurements. Comparatively high levels of esophageal carcinoma associated lincRNA compared to control levels in normal cells can indicate metastasis or poor cancer prognosis. Similarly, comparatively low levels of esophageal carcinoma associated lincRNA compared to control levels in normal cells may indicate cancer progression.

In some embodiments, the level of esophageal adenocarcinoma associated lincRNA, such as lincPRKD, lincRTL, lincMIA, lincNAV, lincTMEM and combinations thereof, can be measured in a bodily sample (e.g., gastric biopsy sample) of a subject to determine a subject having or suspected of having high grade dysplasia and/or esophageal cancer, predict whether the subject has high grade dysplasia and/or esophageal cancer or an increased risk of high grade dysplasia and/or esophageal cancer, determine high grade dysplasia and/or esophageal cancer prognosis in a subject, and/or monitor a subject's response to a treatment regimen for high grade dysplasia and/or esophageal cancer.

Information on levels of a given set of esophageal adenocarcinoma lincRNA thereof obtained using biological samples from individuals afflicted with or at risk of high grade dysplasia and/or esophageal cancer cancer may be grouped to form an expression profile map. The expression profile map can result from the study of a large number of individuals with the same cancer or cancer sub-type. In certain embodiments, a cancer expression profile map is established using samples from individuals with matched age, sex, and body index. Each expression profile map provides a template for comparison to esophageal adenocarcinoma associated lincRNA expression patterns generated from unknown biological samples. Esophageal adenocarcinoma associated lincRNA expression profile maps may be presented as a graphical representation (e.g., on paper or a computer screen), a physical representation (e.g., a gel or array) or a digital representation stored in a computer-readable medium.

As will be appreciated by those of ordinary skill in the art, sets of biomarkers whose expression profiles correlate with cancer may be used to identify, study, or characterize unknown biological samples. Accordingly, in one aspect, methods for characterizing or analyzing biological samples obtained from a subject suspected of having Barrett's esophagus with high grade dysplasia and/or esophageal adenocarcinoma, for diagnosing high grade dysplasia and/or esophageal adenocarcinoma in a subject, and for assessing the responsiveness of high grade dysplasia and/or esophageal adenocarcinoma in a subject to treatment are contemplated. In such methods the esophageal adenocarcinoma associated lincRNA expression levels determined for a biological sample, obtained from the subject, are compared to the levels in one or more control samples. The control samples may be obtained from a healthy individual (or a group of healthy individuals), and/or from an individual (or group of individuals) afflicted with cancer. As mentioned above, the control expression levels of the esophageal adenocarcinoma associated lincRNA of interest are preferably determined from a significant number of individuals, and an average or mean is obtained. In certain aspects, the levels determined for the biological sample under investigation are compared to at least one expression profile map for cancer, as described above.

The methods described herein may be applied to the study of any type of biological samples allowing one or more inventive esophageal adenocarcinoma associated lincRNA to be assayed. Examples of biological samples include, but are not limited to, gastric cells, tissue, or biopsy obtained from the subject using for example endoscopy. In one example, a biological sample device described in WO2015/089422, which is incorporated by reference in its entirety, can be used to collect cell or tissue samples for analysis.

The biological samples used in the practice of the inventive methods may be fresh or frozen samples collected from a subject, or archival samples with known diagnosis, treatment and/or outcome history. Biological samples may be collected by any non-invasive means, such as endoscopy. Preferably, there is enough of the biological sample to accurately and reliably determine the abundance of the set of esophageal adenocarcinoma associated lincRNA of interest. Multiple biological samples may be taken from the subject in order to obtain a representative sampling from the subject.

In some embodiments, the esophageal adenocarcinoma associated lincRNA are extracted from the biological sample before analysis. Methods of RNA extraction are well known in the art (see, for example, J. Sambrook et al., "Molecular Cloning: A Laboratory Manual", 1989, 2nd Ed., Cold Spring Harbor Laboratory Press: Cold Spring Harbor, N.Y.). Most methods of RNA isolation from bodily fluids or tissues are based on the disruption of the tissue in the presence of protein denaturants to quickly and effectively inactivate RNAses. Isolated total RNA may then be further purified from the protein contaminants and concentrated by selective ethanol precipitations, phenol/chloroform extractions followed by isopropanol precipitation or cesium chloride, lithium chloride or cesium trifluoroacetate gradient centrifugations. Kits are also available to extract RNA (i.e., total RNA or mRNA) from bodily fluids or tissues and are commercially available from, for example, Ambion, Inc. (Austin, Tex.), Amersham Biosciences (Piscataway, N.J.), BD Biosciences Clontech (Palo Alto, Calif.), BioRad Laboratories (Hercules, Calif.), GIBCO BRL (Gaithersburg, Md.), and Qiagen, Inc. (Valencia, Calif.).

In certain aspects, after extraction, lincRNA, or mRNA is amplified, and transcribed into cDNA, which can then serve as template for multiple rounds of transcription by the appropriate RNA polymerase Amplification methods are well known in the art (see, for example, A. R. Kimmel and S. L. Berger, Methods Enzymol. 1987, 152: 307-316; J. Sambrook et al., "Molecular Cloning: A Laboratory Manual", 1989, 2nd Ed., Cold Spring Harbour Laboratory Press: New York; "Short Protocols in Molecular Biology", F. M. Ausubel (Ed.), 2002, 5th Ed., John Wiley & Sons; U.S. Pat. Nos. 4,683,195; 4,683,202 and 4,800,159). Reverse transcription reactions may be carried out using non-specific primers, such as an anchored oligo-dT primer, or random sequence primers, or using a target-specific primer complementary to the RNA for each probe being monitored, or using thermostable DNA polymerases (such as avian myeloblastosis virus reverse transcriptase or Moloney murine leukemia virus reverse transcriptase).

The diagnostic methods described herein generally involve the determination of the abundance levels of a plurality (i.e., one or more, e.g., at least 2, at least 3, at least 4, at least 5, at least 6, at least 7, at least 8, at least 9, at least 10 or more) of esophageal adenocarcinoma associated lincRNA in a biological sample obtained from a subject.

It will be appreciated that the diagnostic methods may involve determination of the expression levels of a set of esophageal adenocarcinoma associated lincRNA using any suitable method, including, but not limited to, polymerase chain reaction (PCR) (see, for example, U.S. Pat. Nos. 4,683,195; 4,683,202, and 6,040,166; "PCR Protocols: A Guide to Methods and Applications", Innis et al. (Eds.), 1990, Academic Press: New York), reverse transcriptase PCR(RT-PCT), anchored PCR, competitive PCR (see, for example, U.S. Pat. No. 5,747,251), rapid amplification of cDNA ends (RACE) (see, for example, "Gene Cloning and Analysis: Current Innovations, 1997, pp. 99-115); ligase chain reaction (LCR) (see, for example, EP 01 320308), one-sided PCR (Ohara et al., Proc. Natl. Acad. Sci., 1989, 86: 5673-5677), in situ hybridization, Taqman based assays (Holland et al., Proc. Natl. Acad. Sci., 1991, 88:7276-7280), differential display (see, for example, Liang et al., Nucl. Acid. Res., 1993, 21: 3269-3275) and other RNA fingerprinting techniques, nucleic acid sequence based amplification (NASBA) and other transcription based amplification systems (see, for example, U.S. Pat. Nos. 5,409,818 and 5,554,527), Qbeta Replicase, Strand Displacement Amplification (SDA), Repair Chain Reaction (RCR), nuclease protection assays, subtraction-based methods, Rapid-Scan™, and the like.

Nucleic acid probes for use in the detection of esophageal adenocarcinoma associated lincRNA in biological samples may be constructed using conventional methods known in the art. Suitable probes may be based on nucleic acid sequences, and preferably comprise about 15 to about 50 nucleotides. In some embodiments, the nucleic acid probe can hybridize with or bind to at least one of SEQ ID NOs: 1-12 for the detection of esophageal adenocarcinoma associated lincRNA, such as lincPRKD, lincRTL, lincMIA, lincNAV, or lincTMEM. A nucleic acid probe may be labeled with a detectable moiety, as mentioned above in the case of binding agents. The association between the nucleic acid probe and detectable moiety can be covalent or non-covalent. Detectable moieties can be attached directly to nucleic acid probes or indirectly through a linker (E. S. Mansfield et al., Mol. Cell. Probes, 1995, 9: 145-156). Methods for labeling nucleic acid molecules are well-known in the art (for a review of labeling protocols, label detection techniques and recent developments in the field, see, for example, L. J. Kricka, Ann. Clin. Biochem. 2002, 39: 114-129; R. P. van Gijlswijk et al., Expert Rev. Mol. Diagn. 2001, 1: 81-91; and S. Joos et al., J. Biotechnol. 1994, 35:135-153).

Nucleic acid probes may be used in hybridization techniques to detect esophageal adenocarcinoma associated lincRNA. The technique generally involves contacting an incubating nucleic acid molecules in a biological sample obtained from a subject with the nucleic acid probes under conditions such that specific hybridization takes place between the nucleic acid probes and the complementary sequences in the nucleic acid molecules. After incubation, the non-hybridized nucleic acids are removed, and the presence and amount of nucleic acids that have hybridized to the probes are detected and quantified.

Detection of esophageal adenocarcinoma associated lincRNA may involve amplification of specific polynucleotide sequences using an amplification method such as PCR, followed by analysis of the amplified molecules using techniques known in the art. Suitable primers can be routinely designed by one skilled in the art. In some embodiments, the primers can bind to at least one of SEQ ID NOs: 1-12 for the detection of esophageal adenocarcinoma associated lincRNA, such as lincPRKD, lincRTL, lincMIA, lincNAV, or lincTMEM. In order to maximize hybridization under assay conditions, primers and probes employed in the methods of the invention generally have at least 60%, preferably at least 75% and more preferably at least 90% identity to a portion of nucleic acids.

Hybridization and amplification techniques described herein may be used to assay qualitative and quantitative aspects of expression of nucleic acid molecules comprising polynucleotide sequences coding for the inventive protein markers.

Alternatively, oligonucleotides or longer fragments derived from esophageal adenocarcinoma associated lincRNA may be used as targets in a microarray. A number of different array configurations and methods of their production are known to those skilled in the art (see, for example, U.S. Pat. Nos. 5,445,934; 5,532,128; 5,556,752; 5,242,974; 5,384, 261; 5,405,783; 5,412,087; 5,424,186; 5,429,807; 5,436,327; 5,472,672; 5,527,681; 5,529,756; 5,545,531; 5,554, 501; 5,561,071; 5,571,639; 5,593,839; 5,599,695; 5,624, 711; 5,658,734; and 5,700,637). Microarray technology allows for the measurement of the steady-state level of large numbers of polynucleotide sequences simultaneously. Microarrays currently in wide use include cDNA arrays and oligonucleotide arrays. Analyses using microarrays are generally based on measurements of the intensity of the signal received from a labeled probe used to detect a cDNA sequence from the sample that hybridizes to a nucleic acid probe immobilized at a known location on the microarray (see, for example, U.S. Pat. Nos. 6,004,755; 6,218,114; 6,218,122; and 6,271,002). Array-based gene expression methods are known in the art and have been described in numerous scientific publications as well as in patents (see, for example, M. Schena et al., Science, 1995, 270: 467-470; M. Schena et al., Proc. Natl. Acad. Sci. USA 1996, 93: 10614-10619; Chen et al., Genomics, 1998, 51: 313324;

U.S. Pat. Nos. 5,143,854; 5,445,934; 5,807,522; 5,837, 832; 6,040,138; 6,045,996; 6,284,460; and 6,607,885).

Once the levels of the esophageal adenocarcinoma associated lincRNA of interest have been determined for the biological sample being analyzed, they are compared to the levels in one or more control samples or to at least one expression profile map for cancer described herein. Comparison of levels according to methods of the present invention is preferably performed after the levels obtained have been corrected for both differences in the amount of sample assayed and variability in the quality of the sample used. Correction may be carried out by normalizing the levels against reference genes (e.g., housekeeping genes) in the same sample. Alternatively or additionally, normalization can be based on the mean or median signal (e.g., Ct in the case of RT-PCR) of all assayed genes or a large subset thereof (global normalization approach).

For a given set of esophageal adenocarcinoma associated lincRNA, comparison of an expression pattern obtained for a biological sample against an expression profile map established for cancer may comprise comparison of the normalized levels on a biomarker-by-biomarker (esophageal adenocarcinoma associated lincRNA-by-esophageal adenocarcinoma associated lincRNA) basis and/or comparison of ratios of levels within the set of biomarkers.

Using methods described herein, skilled physicians may select and prescribe treatments adapted to each individual subject based on the diagnosis of a cancer provided to the subject through determination of the levels of the inventive esophageal adenocarcinoma associated lincRNA. In particular, the present invention provides physicians with a non-subjective means to diagnose cancer, which will allow for early treatment, when intervention is likely to have its greatest effect. Selection of an appropriate therapeutic regimen for a given patient may be made based solely on the diagnosis provided by the inventive methods. Alternatively, the physician may also consider other clinical or pathological parameters used in existing methods to diagnose cancer and assess its advancement.

In some embodiments, the methods described herein can be used to select a subject to undergo a therapeutic procedure to ablate Barrett's esophagus with high grade dysplasia if the level of at least one esophageal adenocarcinoma associated lincRNA selected from group consisting of lincPRKD, lincRTL, lincMIA, and lincNAV is upregulated in an esophageal cell or tissue sample from the subject compared to normal tissues or a control. In other embodiments, the methods described herein can be used to select a subject to undergo a therapeutic procedure to ablate Barrett's esophagus with high grade dysplasia if the level of lincTMEM is downregulated in an esophageal cell or tissue sample from the subject compared to normal tissues or a control.

In some embodiments, the methods described herein can be used to select a subject with esophageal adenocarcinoma to undergo chemotherapy or radiation therapy if the level of at least one esophageal adenocarcinoma associated lincRNA selected from group consisting of lincPRKD, lincRTL, lincMIA, and lincNAV is upregulated in an esophageal cancer cell sample from the subject compared to normal tissues or a control. In other embodiments, the methods described herein can be used to select a subject with esophageal adenocarcinoma to undergo chemotherapy or radiation therapy if the level lincTMEM is down regulated in an esophageal cancer cell sample from the subject compared to normal tissues or a control.

In certain embodiments, the assays, methods and systems described herein relate to identifying a subject with esophageal neoplasias that include Barrett's esophagus with high grade dysplasia, or esophageal or gastric cancers (e.g., esophageal adenocarcinoma) or a need for treatment for esophageal neoplasias that include Barrett's esophagus with high grade dysplasia, or esophageal or gastric cancers (e.g., esophageal adenocarcinoma). Certain embodiments are related to assays, methods and systems for identifying the severity of Barrett's esophagus, high grade dysplasia, or esophageal cancers in a sample, e.g., a biopsy sample, obtained from a subject. In some embodiments, where the level of esophageal adenocarcinoma associated lincRNA in the biological sample is at least about 2-fold, at least about 4-fold, at least about 8-fold, or at least about 10-fold increased (e.g., lincPRKD, lincRTL, lincMIA, or lincNAV) as compared to a reference esophageal adenocarcinoma associated lincRNA level, the subject is identified as likely to have high grade dysplasia and/or esophageal adenocarcinoma. In other embodiments, where the level of esophageal adenocarcinoma associated lincRNA in the biological sample is at least about 2-fold, at least about 4-fold, at least about 8-fold, or at least about 10-fold decreased (e.g., lincTMEM) as compared to a reference esophageal adenocarcinoma associated lincRNA level, the subject is identified as likely to have high grade dysplasia and/or esophageal adenocarcinoma. In such instances, a subject identified as likely to have high grade dysplasia and/or esophageal adenocarcinoma can be treated with a more aggressive anti-cancer treatment regimen.

In some embodiments, where the level of esophageal adenocarcinoma associated lincRNA in the biological sample is at least about 2-fold, at least about 4-fold, at least about 8-fold, or at least about 10-fold increased (e.g., lincPRKD, lincRTL, lincMIA, or lincNAV) as compared to a reference esophageal adenocarcinoma associated lincRNA level, the subject is predicted to have a poor outcome and low metastasis free survival, or a decreased survival chance as compared to a subject who has a esophageal adenocarcinoma associated lincRNA levels not statistically significant different or similar to reference esophageal adenocarcinoma associated lincRNA levels. In other embodiments, where the level of esophageal adenocarcinoma associated lincRNA in the biological sample is at least about 2-fold, at least about 4-fold, at least about 8-fold, or at least about 10-fold decreased (e.g., lincTMEM) as compared to a reference esophageal adenocarcinoma associated lincRNA, the subject is predicted to have a poor outcome and low metastasis free survival, or a decreased survival chance as compared to a subject who has a esophageal adenocarcinoma associated lincRNA levels not statistically significant different or similar to reference esophageal adenocarcinoma associated lincRNA levels. In such instances, a subject identified with a poor outcome and low metastasis free survival, or a decreased survival chance can be treated with a more aggressive anti-cancer treatment regimen.

In certain embodiments, the subject may be exhibiting a sign or symptom of Barrett's esophagus, high grade dysplasia, and/or esophageal adenocarcinoma. In certain embodiments, the subject may be asymptomatic or not exhibit a sign or symptom of Barrett's esophagus, high grade dysplasia, and/or esophageal adenocarcinoma, but can be at risk of developing high grade dysplasia and/or esophageal adenocarcinoma due to certain risk factors as described herein.

In some embodiments, the methods and assays described herein include (a) transforming the esophageal adenocarcinoma associated lincRNA into a detectable gene target; (b)

measuring the amount of the detectable gene target; and (c) comparing the amount of the detectable gene target to an amount of a reference, wherein if the amount of the detectable gene target (e.g., esophageal adenocarcinoma associated lincRNA) is statistically different from that of the amount of the reference level for the gene target (e.g., esophageal adenocarcinoma associated lincRNA), the subject is identified as having cancer or is in need of a treatment for cancer.

In some embodiments, the reference can be a level of esophageal adenocarcinoma associated lincRNA in a normal healthy subject with no symptoms or signs of high grade dysplasia and/or esophageal adenocarcinoma. For example, a normal healthy subject who does not have high grade dysplasia and/or esophageal adenocarcinoma. In some embodiments, the reference can also be a level of expression of esophageal adenocarcinoma associated lincRNA in a control sample, a pooled sample of control individuals or a numeric value or range of values based on the same. In some embodiments, the reference can also be a level of the biomarker in a tissue sample taken from non-cancerous tissue of the subject. In certain embodiments, wherein the progression of cancer in a subject is to be monitored over time, the reference can also be a level of high grade dysplasia and/or esophageal adenocarcinoma in a tissue sample taken from the tissue of the subject at an earlier date.

In certain embodiments, esophageal adenocarcinoma associated lincRNA, such as lincPRKD, lincRTL, lincMIA, or lincNAV, is upregulated in a biological sample, e.g., a biopsy sample from a subject with breast cancer. If the level of esophageal adenocarcinoma associated lincRNA is higher than a reference level of that biomarker, the subject is more likely to have high grade dysplasia and/or esophageal adenocarcinoma or to be in need of a treatment for high grade dysplasia and/or esophageal adenocarcinoma. The level of esophageal adenocarcinoma associated lincRNA, which is higher than a reference level for that esophageal adenocarcinoma associated lincRNA, by at least about 10% than the reference amount, at least about 20%, at least about 30%, at least about 40%, at least about 50%, at least about 80%, at least about 100%, at least about 200%, at least about 300%, at least about 500% or at least about 1000% or more, is indicative that the subject has high grade dysplasia and/or esophageal adenocarcinoma.

In other embodiments, an esophageal adenocarcinoma associated lincRNA, such as lincTMEM, is downregulated in a biological sample, e.g., a biopsy sample from a subject with high grade dysplasia and/or esophageal adenocarcinoma. If the level of esophageal adenocarcinoma associated lincRNA is lower than a reference level of that biomarker, the subject is more likely to have cancer or to be in need of a treatment for cancer. The level of an esophageal adenocarcinoma associated lincRNA which is lower than a reference level for that esophageal adenocarcinoma associated lincRNA by at least about 10% than the reference amount, at least about 20%, at least about 30%, at least about 40%, at least about 50%, at least about 80%, at least about 100%, at least about 200%, at least about 300%, at least about 500% or at least about 1000% or more, is indicative that the subject has cancer.

In another embodiment, the assays can include a system for transforming and measuring the amount levels of esophageal adenocarcinoma associated lincRNA as described herein and comparing them to reference expression levels. If the comparison system, which can be a computer implemented system, indicates that the amount of the measured expression product is statistically different from that of the reference amount, the subject from which the sample is collected can be identified as having an increased risk for having cancer or for a subject in need of a treatment for cancer or metastasis.

Systems (and computer readable media for causing computer systems) for performing the methods can include (a) at least one memory containing at least one computer program adapted to control the operation of the computer system to implement a method that includes (i) a determination module configured to identify and detect at the level of esophageal adenocarcinoma associated RNA in a biological sample obtained from a subject; (ii) a storage module configured to store output data from the determination module; (iii) a computing module adapted to identify from the output data whether the level of esophageal adenocarcinoma associated lincRNA measured in the biological sample obtained from a subject varies by a statistically significant amount from the esophageal adenocarcinoma associated lincRNA level found in a esophageal adenocarcinoma associated lincRNA-associated RNA or other markers measured has a statistically significant variation in level in the biological sample obtained from a subject as compared to the reference esophageal adenocarcinoma associated lincRNA and/or displaying the relative expression levels of the biomarkers, e.g., esophageal adenocarcinoma associated lincRNA and (b) at least one processor for executing the computer program.

Embodiments of the invention can be described through functional modules, which are defined by computer executable instructions recorded on computer readable media and which cause a computer to perform method steps when executed. The modules are segregated by function for the sake of clarity. However, it should be understood that the modules/systems need not correspond to discreet blocks of code and the described functions can be carried out by the execution of various code portions stored on various media and executed at various times. Furthermore, it should be appreciated that the modules can perform other functions, thus the modules are not limited to having any particular functions or set of functions.

The computer readable storage media can be any available tangible media that can be accessed by a computer. Computer readable storage media includes volatile and nonvolatile, removable and non-removable tangible media implemented in any method or technology for storage of information such as computer readable instructions, data structures, program modules or other data. Computer readable storage media includes, but is not limited to, RAM (random access memory), ROM (read only memory), EPROM (erasable programmable read only memory), EEPROM (electrically erasable programmable read only memory), flash memory or other memory technology, CD-ROM (compact disc read only memory), DVDs (digital versatile disks) or other optical storage media, magnetic cassettes, magnetic tape, magnetic disk storage or other magnetic storage media, other types of volatile and nonvolatile memory, and any other tangible medium which can be used to store the desired information and which can accessed by a computer including and any suitable combination of the foregoing.

Computer-readable data embodied on one or more computer-readable media may define instructions, for example, as part of one or more programs that, as a result of being executed by a computer, instruct the computer to perform one or more of the functions described herein, and/or various embodiments, variations and combinations thereof. Such instructions may be written in any of a plurality of programming languages, for example, Java, J#, Visual Basic, C, C#, C++, Fortran, Pascal, Eiffel, Basic, COBOL assembly language, and the like, or any of a variety of combinations thereof. The computer-readable media on which such instructions are embodied may reside on one or more of the components of either of a system, or a computer readable storage medium described herein, may be distributed across one or more of such components.

The computer-readable media may be transportable such that the instructions stored thereon can be loaded onto any computer resource to implement the aspects discussed herein. In addition, it should be appreciated that the instructions stored on the computer-readable medium, described above, are not limited to instructions embodied as part of an application program running on a host computer. Rather, the instructions may be embodied as any type of computer code (e.g., software or microcode) that can be employed to program a computer to implement aspects of the present invention. The computer executable instructions may be written in a suitable computer language or combination of several languages. Basic computational biology methods are known to those of ordinary skill in the art and are described in, for example, Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001).

The functional modules of certain embodiments of the invention include at minimum a determination module, a storage module, a computing module, and a display module. The functional modules can be executed on one, or multiple, computers, or by using one, or multiple, computer networks. The determination module has computer executable instructions to provide e.g., levels of expression products etc in computer readable form.

The determination module can comprise any system for detecting a signal elicited from the esophageal adenocarcinoma associated lincRNA described herein in a biological sample. In some embodiments, such systems can include an instrument, e.g., StepOnePlus Real-Time PCR systems (Applied Biosystems) as described herein for quantitative RT-PCR. In another embodiment, the determination module can comprise multiple units for different functions, such as amplification and hybridization. In one embodiment, the determination module can be configured to perform the quantitative RT-PCR methods described in the Examples, including amplification, detection, and analysis.

The information determined in the determination system can be read by the storage module. As used herein the "storage module" is intended to include any suitable computing or processing apparatus or other device configured or adapted for storing data or information. Examples of electronic apparatus suitable for use with the present invention include stand-alone computing apparatus, data telecommunications networks, including local area networks (LAN), wide area networks (WAN), Internet, Intranet, and Extranet, and local and distributed computer processing systems. Storage modules also include, but are not limited to: magnetic storage media, such as floppy discs, hard disc storage media, magnetic tape, optical storage media such as CD-ROM, DVD, electronic storage media such as RAM, ROM, EPROM, EEPROM and the like, general hard disks and hybrids of these categories such as magnetic/optical storage media. The storage module is adapted or configured for having recorded thereon, for example, sample name, alleleic variants, and frequency of each alleleic variant. Such information may be provided in digital form that can be transmitted and read electronically, e.g., via the Internet, on diskette, via USB (universal serial bus) or via any other suitable mode of communication.

As used herein, "stored" refers to a process for encoding information on the storage module. Those skilled in the art can readily adopt any of the presently known methods for recording information on known media to generate manufactures comprising expression level information.

The "computing module" can use a variety of available software programs and formats for computing the relative expression level of the esophageal adenocarcinoma associated lincRNA described herein. Such algorithms are well established in the art. A skilled artisan is readily able to determine the appropriate algorithms based on the size and quality of the sample and type of data. By way of an example, when the level of esophageal adenocarcinoma associated lincRNA in a biological sample obtained from a subject is measured, a comparison module can compare or match the output data—with a reference esophageal adenocarcinoma associated lincRNA level in a reference sample. In certain embodiments, the reference expression level can have been pre-stored in the storage module. During the comparison or matching process, the comparison module can determine whether the expression level in the tissue sample obtained from a subject is lower than the reference expression level to a statistically significant degree. In various embodiments, the comparison module can be configured using existing commercially-available or freely-available software for comparison purpose, and may be optimized for particular data comparisons that are conducted.

The computing and/or comparison module, or any other module of the invention, can include an operating system (e.g., UNIX) on which runs a relational database management system, a World Wide Web application, and a World Wide Web server. World Wide Web application includes the executable code necessary for generation of database language statements (e.g., Structured Query Language (SQL) statements). Generally, the executables will include embedded SQL statements. In addition, the World Wide Web application may include a configuration file, which contains pointers and addresses to the various software entities that comprise the server as well as the various external and internal databases which must be accessed to service user requests. The Configuration file also directs requests for server resources to the appropriate hardware—as may be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GenBank or Swiss Pro World Wide Web site). Thus, in a particular preferred embodiment of the present invention, users can directly access data (via Hypertext links for example) residing on Internet databases using a HTML interface provided by Web browsers and Web servers.

The computing and/or comparison module provides a computer readable comparison result that can be processed in computer readable form by predefined criteria, or criteria defined by a user, to provide content based in part on the comparison result that may be stored and output as requested by a user using an output module, e.g., a display module.

In certain embodiments, the content displayed on the display module can indicate whether the esophageal adenocarcinoma associated lincRNA measured have a statistically significant variation in expression (e.g., increase or decrease) between the biological sample obtained from a subject as compared to a reference expression level. In certain embodiments, the content displayed on the display module can indicate the degree to which the esophageal adenocarcinoma associated lincRNA were found to have a statistically significant variation in expression between the biological sample obtained from a subject as compared to a reference expression level. In certain embodiments, the content displayed on the display module can indicate whether the subject has an increased risk of having cancer, and/or the severity of the cancer. In certain embodiments, the content displayed on the display module can indicate whether the subject is in need of a treatment for cancer. In certain embodiments, the content displayed on the display module can indicate whether the subject has an increased risk of having a more severe case of cancer or metastasis. In some embodiments, the content displayed on the display module can be a numerical value indicating one of these risk or probabilities. In such embodiments, the probability can be expressed in percentages or a fraction.

Other embodiments described herein relate to an agent effective to decrease, reduce or downregulate the level of esophageal adenocarcinoma associated lincRNA that is over-expressed or upregulated in the cancer cells compared to normal cells. As used herein, the term "downregulate", or "reduce", means that the level of esophageal adenocarcinoma associated lincRNA molecules or equivalent RNA is reduced below that observed in comparative normal cells. The esophageal adenocarcinoma associated lincRNA is downregulated when expression of the esophageal adenocarcinoma associated lincRNA molecules is reduced at least 10%, at least about 20%, at least about 30%, at least about 50%, or at least about 75% relative to a corresponding non-modulated control. Thus, in some embodiments, the agent can be an inhibitor (e.g., antagonist) of esophageal adenocarcinoma associated lincRNA that is upregulated or over expressed in the cancer cells compared to normal cells.

In one example, the esophageal adenocarcinoma associated lincRNA that is over expressed can include at least one of lincPRKD, lincRTL, lincMIA, or lincNAV.

An inhibitor of esophageal adenocarcinoma associated lincRNA, which is upregulated or over expressed in esophageal cells or esophageal cancer cells compared to normal cells, can include any agent that inhibits or reduces esophageal adenocarcinoma associated lincRNA expression or function. Agents that inhibit or reduce esophageal adenocarcinoma associated lincRNA expression or function can be any type of entity, for example, chemicals, nucleic acid sequences, nucleic acid analogues, proteins, peptides or fragments thereof. In some embodiments, the agent is any chemical, entity or moiety, including without limitation, synthetic and naturally-occurring non-proteinaceous entities. In certain embodiments the agent is a small molecule having a chemical moiety.

In some embodiments, agents that inhibit or reduce esophageal adenocarcinoma associated lincRNA expression or function are nucleic acids. Nucleic acid inhibitors of esophageal adenocarcinoma associated lincRNA expression or function include, for example, RNA interference (RNAi) molecules or constructs, such as siRNA, dsRNA, stRNA, shRNA, microRNA and modified versions thereof, where the RNA interference molecule silences the expression or function of the esophageal adenocarcinoma associated lincRNA. The RNAi molecule of esophageal adenocarcinoma associated lincRNA can have nucleic acid sequence that is substantially complementary to a portion of at least one esophageal adenocarcinoma associated lincRNA that is upregulated in the cancer cells. For example, the RNAi molecule of esophageal adenocarcinoma associated lincRNA can have nucleic acid sequence that is substantially complementary to a portion of at least one esophageal adenocarcinoma associated lincRNA selected from the group consisting of lincPRKD, lincRTL, lincMIA, or lincNAV.

In some embodiments single-stranded RNA (ssRNA), a form of RNA endogenously found in eukaryotic cells can be used to form an RNAi molecule. Cellular ssRNA molecules include messenger RNAs (and the progenitor pre-messenger RNAs), small nuclear RNAs, small nucleolar RNAs, transfer RNAs and ribosomal RNAs. Double-stranded RNA (dsRNA) induces a size-dependent immune response such that dsRNA larger than 30 bp activates the interferon response, while shorter dsRNAs feed into the cell's endogenous RNA interference machinery downstream of the Dicer enzyme.

RNA interference (RNAi) provides a powerful approach for inhibiting the expression of selected target RNAs. RNAi uses small interfering RNA (siRNA) duplexes that target the RNA for selective degradation. siRNA-dependent post-transcriptional silencing of gene expression involves cutting the target messenger RNA molecule at a site guided by the siRNA.

RNA interference (RNAi) is an evolutionarily conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn, G. and Cullen, B. (2002) J. of Virology 76(18): 9225), thereby inhibiting expression of the target gene. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex (termed "RNA induced silencing complex," or "RISC") that recognizes and cleaves target mRNAs. RNAi can also be initiated by introducing nucleic acid molecules, e.g., synthetic siRNAs or RNA interfering agents, to inhibit or silence the expression of target genes. As used herein, "inhibition of target gene expression" includes any decrease in expression or level of the target gene as compared to a situation wherein no RNA interference has been induced. The decrease can be of at least about 30%, 40%, 50%, 60%, 70%, 80%, 90%, 95% or 99% or more as compared to the expression of a target gene or the activity or level of the protein encoded by a target gene which has not been targeted by an RNA interfering agent.

"Short interfering RNA" (siRNA), also referred to herein as "small interfering RNA" refers to an agent which functions to inhibit expression of a target gene, e.g., by RNAi. An siRNA can be chemically synthesized, can be produced by in vitro transcription, or can be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, 22, or 23 nucleotides in length, and can contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

siRNAs also include small hairpin (also called stem loop) RNAs (shRNAs). In one embodiment, these shRNAs are composed of a short (e.g., about 19 to about 25 nucleotide) antisense strand, followed by a nucleotide loop of about 5 to about 9 nucleotides, and the analogous sense strand. Alternatively, the sense strand can precede the nucleotide loop structure and the antisense strand can follow. These shRNAs can be contained in plasmids, retroviruses, and lentiviruses and expressed from, for example, the pol III U6 promoter, or another promoter (see, e.g., Stewart, et al. (2003) RNA April; 9(4):493-501, incorporated by reference herein in its entirety).

A siRNA can be substantially homologous to the target gene or genomic sequence, or a fragment thereof. As used in this context, the term "homologous" is defined as being substantially identical, sufficiently complementary, or similar to the target mRNA, or a fragment thereof, to effect RNA interference of the target. In addition to native RNA molecules, RNA suitable for inhibiting or interfering with the expression of a target sequence include RNA derivatives and analogs.

The siRNA targets only one sequence. Each of the RNA interfering agents, such as siRNAs, can be screened for potential off-target effects by, for example, expression profiling. Such methods are known to one skilled in the art and are described, for example, in Jackson et al, Nature Biotechnology 6:635-637, 2003. In addition to expression profiling, one can also screen the potential target sequences for similar sequences in the sequence databases to identify potential sequences which can have off-target effects. For example, according to Jackson et al. (Id.) 15, or perhaps as few as 11 contiguous nucleotides of sequence identity are sufficient to direct silencing of non-targeted transcripts. Therefore, one can initially screen the proposed siRNAs to avoid potential off-target silencing using the sequence identity analysis by any known sequence comparison methods, such as BLAST.

siRNA molecules need not be limited to those molecules containing only RNA, but, for example, further encompass chemically modified nucleotides and non-nucleotides, and also include molecules wherein a ribose sugar molecule is substituted for another sugar molecule or a molecule which performs a similar function. Moreover, a non-natural linkage between nucleotide residues can be used, such as a phosphorothioate linkage. For example, siRNA containing D-arabinofuranosyl structures in place of the naturally-occurring D-ribonucleosides found in RNA can be used in RNAi molecules according to the present invention (U.S. Pat. No. 5,177,196).

The RNA strand can be derivatized with a reactive functional group of a reporter group, such as a fluorophore. Particularly useful derivatives are modified at a terminus or termini of an RNA strand, typically the 3' terminus of the sense strand. For example, the 2'-hydroxyl at the 3' terminus can be readily and selectively derivatized with a variety of groups.

Other useful RNA derivatives incorporate nucleotides having modified carbohydrate moieties. The RNA bases can also be modified. Any modified base useful for inhibiting or interfering with the expression of a target sequence can be used. For example, halogenated bases, such as 5-bromouracil and 5-iodouracil can be incorporated. The bases can also be alkylated, for example, 7-methylguanosine can be incorporated in place of a guanosine residue. Non-natural bases that yield successful inhibition can also be incorporated.

siRNA and miRNA molecules having various "tails" covalently attached to either their 3'- or to their 5'-ends, or to both, are also known in the art and can be used to stabilize the siRNA and miRNA molecules delivered using the methods of the present invention. Generally speaking, intercalating groups, various kinds of reporter groups and lipophilic groups attached to the 3' or 5' ends of the RNA molecules are well known to one skilled in the art and are useful according to the methods of the present invention. Descriptions of syntheses of 3'-cholesterol or 3'-acridine modified oligonucleotides applicable to preparation of modified RNA molecules useful according to the present invention can be found, for example, in the articles: Gamper, H. B., Reed, M. W., Cox, T., Virosco, J. S., Adams, A. D., Gall, A., Scholler, J. K., and Meyer, R. B. (1993) Facile Preparation and Exonuclease Stability of 3'-Modified Oligodeoxynucleotides. Nucleic Acids Res. 21 145-150; and Reed, M. W., Adams, A. D., Nelson, J. S., and Meyer, R. B., Jr. (1991) Acridine and Cholesterol-Derivatized Solid Supports for Improved Synthesis of 3'-Modified Oligonucleotides. Bioconjugate Chem. 2 217-225 (1993).

Other siRNAs useful for targeting esophageal adenocarcinoma associated lincRNA expression or function can be readily designed and tested. Accordingly, siRNAs useful for the methods described herein include siRNA molecules of about 15 to about 40 or about 15 to about 28 nucleotides in length. In some embodiments, the esophageal adenocarcinoma associated lincRNA targeting siRNA molecules can have a length of about 25 to about 29 nucleotides. In other embodiments, the esophageal adenocarcinoma associated lincRNA targeting siRNA molecules have a length of about 27, 28, 29, or 30 nucleotides. The esophageal adenocarcinoma associated lincRNA targeting siRNA molecules can also comprise a 3' hydroxyl group. The esophageal adenocarcinoma associated lincRNA targeting siRNA molecules can be single-stranded or double stranded; such molecules can be blunt ended or comprise overhanging ends (e.g., 5', 3'). In specific embodiments, the RNA molecule is double stranded and either blunt ended or comprises overhanging ends.

In some embodiments, the siRNA or modified siRNA, such as gene silencing RNAi agents, and/or gene activating RNAi agents are delivered in a pharmaceutically acceptable carrier. Additional carrier agents, such as liposomes, can be added to the pharmaceutically acceptable carrier.

In another embodiment, the siRNA is delivered by delivering a vector encoding small hairpin RNA (shRNA) in a pharmaceutically acceptable carrier to the cells in an organ of an individual. The shRNA is converted by the cells after transcription into siRNA capable of targeting, for example, the esophageal adenocarcinoma associated lincRNA, to inhibit its function and/or expression. In one embodiment, the vector can be a regulatable vector, such as tetracycline inducible vector.

In one embodiment, the RNA interfering agents used in the methods described herein are taken up actively by cells in vivo following intravenous injection, e.g., hydrodynamic injection, without the use of a vector, illustrating efficient in vivo delivery of the RNA interfering agents, e.g., the siRNAs used in the methods described herein.

Other strategies for delivery of the RNA interfering agents, e.g., the siRNAs or shRNAs used in the methods described herein, can also be employed, such as, for example, delivery by a vector, e.g., a plasmid or viral vector, e.g., a lentiviral vector. Such vectors can be used as described, for example, in Xiao-Feng Qin et al. Proc. Natl. Acad. Sci. U.S.A., 100: 183-188. Other delivery methods include delivery of the RNA interfering agents, e.g., the siRNAs or shRNAs, using a basic peptide by conjugating or mixing the RNA interfering agent with a basic peptide, e.g., a fragment of a TAT peptide, mixing with cationic lipids or formulating into particles.

As noted, the dsRNA, such as siRNA or shRNA can be delivered using an inducible vector, such as a tetracycline inducible vector. Methods described, for example, in Wang et al. Proc. Natl. Acad. Sci. 100: 5103-5106, using pTet-On vectors (BD Biosciences Clontech, Palo Alto, Calif.) can be used. In some embodiments, a vector can be a plasmid vector, a viral vector, or any other suitable vehicle adapted for the insertion and foreign sequence and for the introduction into eukaryotic cells. The vector can be an expression vector capable of directing the transcription of the DNA sequence of the agonist or antagonist nucleic acid molecules into RNA. Viral expression vectors can be selected from a group comprising, for example, reteroviruses, lentiviruses, Epstein Barr virus-, bovine papilloma virus, adenovirus- and adeno-associated-based vectors or hybrid virus of any of the above. In one embodiment, the vector is episomal. The use of an episomal vector provides a means of maintaining the antagonist nucleic acid molecule in the subject in high copy number extra chromosomal DNA thereby eliminating potential effects of chromosomal integration.

RNA interference molecules and nucleic acid inhibitors used in the methods as disclosed herein can be produced using any known techniques, such as direct chemical synthesis, through processing of longer double stranded RNAs by exposure to recombinant Dicer protein or Drosophila embryo lysates, through an in vitro system derived from S2 cells, using phage RNA polymerase, RNA-dependant RNA polymerase, and DNA based vectors. Use of cell lysates or in vitro processing can further involve the subsequent isolation of the short, for example, about 21-23 nucleotide, siRNAs from the lysate, etc. Chemical synthesis usually proceeds by making two single stranded RNA-oligomers followed by the annealing of the two single stranded oligomers into a double stranded RNA. Other examples include methods disclosed in WO 99/32619 and WO 01/68836 that teach chemical and enzymatic synthesis of siRNA. Moreover, numerous commercial services are available for designing and manufacturing specific siRNAs (see, e.g., QIAGEN Inc., Valencia, Calif. and AMBION Inc., Austin, Tex.)

In one embodiment, an inhibitor of esophageal adenocarcinoma associated lincRNA function and/or its expression can be obtained synthetically, for example, by chemically synthesizing a nucleic acid by any method of synthesis known to the skilled artisan. A synthesized nucleic acid inhibitor of esophageal adenocarcinoma associated lincRNA function and/or its expression can then be purified by any method known in the art. Methods for chemical synthesis of nucleic acids include, but are not limited to, in vitro chemical synthesis using phosphotriester, phosphate or phosphoramidite chemistry and solid phase techniques, or via deoxynucleoside H-phosphonate intermediates (see U.S. Pat. No. 5,705,629 to Bhongle).

Synthetic siRNA molecules, including shRNA molecules, can also easily be obtained using a number of techniques known to those of skill in the art. For example, the siRNA molecule can be chemically synthesized or recombinantly produced using methods known in the art, such as using appropriately protected ribonucleoside phosphoramidites and a conventional DNA/RNA synthesizer (see, e.g., Elbashir, S. M. et al. (2001) Nature 411:494-498; Elbashir, S. M., W. Lendeckel and T. Tuschl (2001) Genes & Development 15:188-200; Harborth, J. et al. (2001) J. Cell Science 114:4557-4565; Masters, J. R. et al. (2001) Proc. Natl. Acad. Sci., USA 98:8012-8017; and Tuschl, T. et al. (1999) Genes & Development 13:3191-3197). Alternatively, several commercial RNA synthesis suppliers are available including, but are not limited to, Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK). As such, siRNA molecules are not overly difficult to synthesize and are readily provided in a quality suitable for RNAi. In addition, dsRNAs can be expressed as stem loop structures encoded by plasmid vectors, retroviruses and lentiviruses (Paddison, P. J. et al. (2002) Genes Dev. 16:948-958; McManus, M. T. et al. (2002) RNA 8:842-850; Paul, C. P. et al. (2002) Nat. Biotechnol. 20:505-508; Miyagishi, M. et al. (2002) Nat. Biotechnol. 20:497-500; Sui, G. et al. (2002) Proc. Natl. Acad. Sci., USA 99:5515-5520; Brummelkamp, T. et al. (2002) Cancer Cell 2:243; Lee, N. S., et al. (2002) Nat. Biotechnol. 20:500-505; Yu, J. Y., et al. (2002) Proc. Natl. Acad. Sci., USA 99:6047-6052; Zeng, Y., et al. (2002) Mol. Cell. 9:1327-1333; Rubinson, D. A., et al. (2003) Nat. Genet. 33:401-406; Stewart, S. A., et al. (2003) RNA 9:493-501). These vectors generally have a polIII promoter upstream of the dsRNA and can express sense and antisense RNA strands separately and/or as a hairpin structures. Within cells, Dicer processes the short hairpin RNA (shRNA) into effective siRNA.

Methods of delivering RNAi agents, e.g., a siRNA, or vectors containing an RNAi agent, to the target cells (e.g., colon cancer cells, breast cancer cells, or other desired target cells) are well known to persons of ordinary skill in the art. In some embodiments, a RNAi agent inhibitor of esophageal adenocarcinoma associated lincRNA function and/or its expression can be administered to a subject by injection of a composition containing the RNA interfering agent, e.g., an siRNA, or directly contacting the cell with a composition comprising an RNAi agent, e.g., an siRNA. In another embodiment, RNAi agents, e.g., a siRNA can be injected directly into any blood vessel, such as vein, artery, venule or arteriole, via, e.g., hydrodynamic injection or catheterization.

Administration can be by a single injection or by two or more injections. In some embodiments, a RNAi agent is delivered in a pharmaceutically acceptable carrier. A gene silencing-RNAi agent, which inhibits esophageal adenocarcinoma associated lincRNA function and/or its expression can also be administered in combination with other pharmaceutical agents which are used to treat or prevent cancer.

In one embodiment, specific cells are targeted with RNA interference, limiting potential side effects of RNA interference caused by non-specific targeting of RNA interference. The method can use, for example, a complex or a fusion molecule comprising a cell targeting moiety and an RNA interference binding moiety that is used to deliver RNAi effectively into cells. In some embodiments, a siRNA or RNAi binding moiety is a protein or a nucleic acid binding domain or fragment of a protein, and the binding moiety is fused to a portion of the targeting moiety. The location of the targeting moiety can be either in the carboxyl-terminal or amino-terminal end of the construct or in the middle of the fusion protein.

In some embodiments, a viral-mediated delivery mechanism can also be employed to deliver siRNAs, e.g., siRNAs (e.g., gene silencing-RNAi agents) which inhibits esophageal adenocarcinoma associated lincRNA function and/or its expression to cells in vitro and in vivo as described in Xia, H. et al. (2002) Nat Biotechnol 20(10):1006). Plasmid- or viral-mediated delivery mechanisms of shRNA can also be employed to deliver shRNAs to cells in vitro and in vivo as described in Rubinson, D. A., et al. ((2003) Nat. Genet. 33:401-406) and Stewart, S. A., et al. ((2003) RNA 9:493-501).

The dose of the particular RNAi agent will be in an amount necessary to effect RNA interference, e.g., gene silencing RNAi which inhibits esophageal adenocarcinoma associated lincRNA function and/or its expression leading to reduction of esophageal adenocarcinoma associated lincRNA level.

In other embodiments, an agent that modulates the level of esophageal adenocarcinoma associated lincRNA in the esophageal cancer cells of the subject can be an agent that increases, enhances or upregulates the level of esophageal adenocarcinoma associated lincRNA, which is under-expressed or downregulated in the cancer cells compared to normal cells. The agent can include, for example, a nucleic acid encoding the under expressed or downregulated esophageal adenocarcinoma associated lincRNA in the cancer cells.

In one example, the esophageal adenocarcinoma associated lincRNA that is under expressed or downregulated in the cancer cells can include lincTMEM.

In some embodiments, a nucleic acid encoding the esophageal adenocarcinoma associated lincRNA can be substantially homologous or have a sequence identity that is substantially identical to native (or nonmutated) esophageal adenocarcinoma associated lincRNA such that when the nucleic acid encoding the esophageal adenocarcinoma associated lincRNA is administered to cancer cells of the subject, cancer growth, proliferation and/or metastasis is inhibited or reduced. By substantially homologous, it is meant the esophageal adenocarcinoma associated lincRNA has an at least about 80%, about 90%, about 95%, about 96%, about 97%, about 98%, about 99% or about 100% sequence identity with the nucleotide sequence of the native (or nonmutated) esophageal adenocarcinoma associated lincRNA.

In some embodiments, a nucleic acid encoding the downregulated esophageal adenocarcinoma associated lincRNA can have a nucleic acid sequence substantially homologous to the esophageal adenocarcinoma associated lincRNA or corresponding nucleic acid sequence of lincTMEM. The nucleic encoding the esophageal adenocarcinoma associated lincRNA can be administered to cells through gene therapy using, for example, a nucleic acid construct. In general, there are two approaches to gene therapy in humans. For in vivo gene therapy, a nucleic acid construct encoding the nucleic acid or polynucleotide of interest can be administered directly to the subject or cells. Alternatively, in ex vivo gene therapy, cells are removed from the subject and treated with a nucleic acid construct to express the gene of interest. In the ex vivo method of gene therapy, the treated cells are then re-administered to the patient.

Numerous different methods for gene therapy are well known in the art. These methods include, but are not limited to, the use of nucleic acid constructs provided in DNA plasmid vectors as well as DNA and RNA viral vectors. These vectors are engineered to express esophageal adenocarcinoma associated RNA when integrated into patient cells.

Additionally, nucleic acid constructs for use in methods described herein may have expression signals, such as a strong promoter, a strong termination codon, adjustment of the distance between the promoter and the cloned gene, and the insertion of a transcription termination sequence.

In certain aspects, the nucleic acid construct includes a nucleic acid substantially homologous to esophageal adenocarcinoma associated lincRNA operably linked to a promoter to facilitate esophageal adenocarcinoma associated RNA expression within a cancer cell. The promoter may be a strong, viral promoter that functions in eukaryotic cells such as a promoter derived from cytomegalovirus (CMV), simian virus 40 (SV40), mouse mammary tumor virus (MMTV), Rous sarcoma virus (RSV), or adenovirus.

Alternatively, the promoter used may be tissue-specific, cell type-specific promoter, or a strong general eukaryotic promoter, such as the actin gene promoter. In another aspect, the promoter is a regulated promoter, such as a tetracycline-regulated promoter, expression from which can be regulated by exposure to an exogenous substance (e.g., tetracycline).

Introduction of one or more of the nucleic acid construct(s) including a nucleic acid encoding a esophageal adenocarcinoma associated lincRNA can be achieved using a variety of gene transfer protocols permitting transfection of the nucleic acid construct into the cells. Genetic change can be accomplished either by incorporation of the new nucleic acid into the genome of the host cell, or by transient or stable maintenance of the new DNA as an episomal element. A cell has been "transfected" when the nucleic acid construct has been introduced inside the cell membrane using any technology used to introduce nucleic acid molecules into cells.

A number of transfection techniques are well known in the art and are disclosed herein. See, for example, Graham et al., Virology, 52: 456 (1973); Sambrook et al., Molecular Cloning, a laboratory Manual, Cold Spring Harbor Laboratories (New York, 1989); Davis et al., Basic Methods in Molecular Biology, Elsevier, 1986; and Chu et al., Gene, 13: 197 (1981). Such techniques can be used to introduce one or more nucleic acid constructs described herein into the cells.

In some aspects, the nucleic acid construct can be introduced into cancer cells using a viral vector. The precise vector and vector formulation used will depend upon several factors, such as the size of the nucleic acid construct to be transferred and the delivery protocol to be used. The nucleic acid construct can also be introduced as infectious particles, e.g., DNA-ligand conjugates, calcium phosphate precipitates, and liposomes.

In general, viral vectors used are composed of a viral particle derived from a naturally occurring virus, which has been genetically altered to render the virus replication-defective and to deliver a recombinant gene of interest for expression in a target cell. Numerous viral vectors are well known in the art, including, for example, retrovirus, lentivirus, adenovirus, adeno-associated virus, herpes simplex virus (HSV), cytomegalovirus (CMV), vaccinia and poliovirus vectors. The viral vector may be selected according to its preferential infection of the cells targeted.

Where a replication-deficient virus is used as the viral vector, the production of infectious virus particles containing either DNA or RNA corresponding to the nucleic acid construct can be achieved by introducing the viral construct into a recombinant cell line, which provides the missing components essential for viral replication. Transformation of the recombinant cell line with the recombinant viral vector will not result in production or substantial production of replication-competent viruses, e.g., by homologous recombination of the viral sequences of the recombinant cell line into the introduced viral vector. Methods for production of replication-deficient viral particles containing a nucleic acid of interest are well known in the art and are described in, for example, Rosenfeld et al., Science 252:431-434, 1991 and Rosenfeld et al., Cell 68:143-155, 1992 (adenovirus); U.S. Pat. No. 5,139,941 (adeno-associated virus); U.S. Pat. No. 4,861,719 (retrovirus); and U.S. Pat. No. 5,356,806 (vaccinia virus).

In other embodiments, the nucleic acid construct including a nucleic acid encoding a esophageal adenocarcinoma associated lincRNA may be introduced into a cell using a non-viral vector. "Non-viral vector" as used herein is meant to include naked RNA (e.g., RNA not contained within a viral particle, and free of a carrier molecules such as lipids), chemical formulations comprising naked nucleic acid (e.g., a formulation of RNA (and/or DNA) and cationic compounds (e.g., dextran sulfate, cationic lipids)), and naked nucleic acid mixed with an adjuvant, such as a viral particle (e.g., the DNA or RNA of interest is not contained within the viral particle, but the formulation is composed of both naked DNA and viral particles (e.g., adenovirus particles) (see, e.g., Curiel et al. 1992 Am. J. Respir. Cell Mol. Biol. 6:247-52). Thus, "non-viral vector" can include vectors composed of nucleic acid plus viral particles where the viral particles do not contain the nucleic acid construct within the viral genome.

In some aspects, a liposome non-viral vector can be used to introduce the nucleic acid encoding the esophageal adenocarcinoma associated lincRNA into the cell. Liposomes for use in the method described herein can include a mixture of lipids, which bind to the nucleic acid construct and facilitate delivery of the construct into the cell. Examples of liposomes that can be used include DOPE (dioleyl phosphatidyl ethanol amine), CUDMEDA (N-(5-cholestrum-3-β-ol 3-urethanyl)-N1,N1-dimethylethylene diamine).

The nucleic acid encoding the esophageal adenocarcinoma associated lincRNA or vector thereof can be incorporated into pharmaceutical compositions suitable for administration to a subject. In some particular embodiments, the pharmaceutical composition comprises the vectors described herein and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it can be preferable to include isotonic agents, for example, sugars, polyalcohols such as mannitol, sorbitol, or sodium chloride in the composition. Pharmaceutically acceptable carriers can further comprise minor amounts of auxiliary substances, such as wetting or emulsifying agents, preservatives or buffers, which enhance the shelf life or effectiveness of the vector or pharmaceutical composition.

The compositions described herein may be in a variety of forms. These include, for example, liquid, semi-solid and solid dosage forms, such as liquid solutions (e.g., injectable and infusible solutions, dispersions or suspensions, tablets, pills, powders, liposomes and suppositories. The form used depends on the intended mode of administration and therapeutic application. Typical compositions are in the form of injectable or infusible solutions.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the vector in the required amount in an appropriate solvent with one or a combination of ingredients enumerated above, as required, followed by filtered sterilization.

Generally, dispersions are prepared by incorporating the vector into a sterile vehicle that contains a basic dispersion medium and the required other ingredients from those enumerated above. In the case of sterile lyophilized powders for the preparation of sterile injectable solutions, the methods of preparation can include vacuum drying and spray-drying that yields a powder of the active ingredient plus any additional desired ingredient from a previously sterile-filtered solution thereof. The proper fluidity of a solution can be maintained, for example, by the use of a coating, such as lecithin, by the maintenance of the required particle size in the case of dispersion and by the use of surfactants. Prolonged absorption of injectable compositions can be achieved by including an agent in the composition that delays absorption, for example, monostearate salts and gelatin.

The vectors described herein can be administered by a variety of methods known in the art. As will be appreciated by the skilled artisan, the route and/or mode of administration will vary depending upon the desired results. In certain embodiments, the vector may be prepared with a carrier that will protect the vector against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are generally known to those skilled in the art.

In some embodiments, one or more agents that decrease the level of esophageal adenocarcinoma associated lincRNA that is upregulated in the cancer cells and/or agents that increase the level of esophageal adenocarcinoma associated lincRNA that is downregulated in the cancer cells can be administered to cancer cells of the subject at an amount effective to modulate the level of esophageal adenocarcinoma associated lincRNA and/or the interaction of esophageal adenocarcinoma associated lincRNA in the esophageao cancer cells of the subject and treat esophageal cancer.

Other embodiments relate to a nucleic acid construct of esophageal adenocarcinoma associated lincRNA selected from the group consisting lincRTL (SEQ ID NO: 1), lincMIA (SEQ ID NO: 2, SEQ ID NO: 3, SEQ ID NO: 4, or SEQ ID NO: 5), lincPRKD (SEQ ID NO: 6, SEQ ID NO:7, SEQ ID NO: 8, SEQ ID NO: 9, SEQ ID NO: 10), lincTMEM (SEQ ID NO: 11 or SEQ ID NO: 12) or a fragment of at least 20 bp thereof. In some embodiments, nucleic acid construct can be used in designing nucleic acid probes and primers for detecting or measuring the levels of esophageal adenocarcinoma associated lincRNA as well as designing expression vectors and interfering RNA for treating esophageal adenocarcinoma.

Example

In this Example, we identified and characterized lincRNAs in the Barrett's disease model. We innovatively used RNA sequencing to genome-wide profile the expression of 8000 lincRNAs in 56 pre-treatment esophageal adenocarcinoma (EAC) biopsies, 18 Barrett's esophageal (BE) lesions obtained from patients with no history of dysplasia or cancer development (median surveillance of 9 years, ranging from 6 to 22 years), 20 normal SQ biopsies matching 20 of the EAC cases, and 11 normal gastric (GAST) biopsy samples. Using a stringent selection criteria, we identified five novel lincRNAs, lincPRKD, lincRTL, lincMIA, lincNAV, and lincTMEM, as markedly deregulated in EACs. We further confirmed the differential expression of these lincRNAs using quantitative real-time PCR (qPCR) (FIG. 1). Together, deregulations in these 5 candidates accounted for >80% of the EAC cases with each lincRNA showing alterations in at least 30% of EACs. Furthermore, our phenotypic analyses in EAC cell line models using antisense molecules against two of the candidate lincRNAs, Onco-lincPRKD and Onco-lincRTL, showed marked growth suppression of esophageal adenocarcinoma cells (FIG. 2), strongly supporting a critical role for these candidate lincRNAs in EAC progression.

The example shows the characterization of global lincRNA deregulations in the Barrett's disease model. More importantly, we identified these novel lincRNAs as having a role in esophageal carcinogenesis, as novel biomarkers of malignant progression of BE, and as novel therapeutic targets for BE with high-grade dysplasia and esophageal adenocarcinomas.

Specifically, increased levels of the four Onco-lincRNA markers and decreased levels of one Suppressor-lincRNA markers (FIG. 1) in tissues from BE patients, as well as our findings suggesting an important tumorigenic role for these lincRNAs in Barrett's neoplasia (FIG. 2), may be used to select patients to undergo a diagnostic procedure for detection of Barrett's esophagus with high grade dysplasia or esophageal cancer; for surveillance of disease progression in individuals that have BE and in identifying BE patients who need therapeutic ablation; to identify patients who will respond to the standard chemo-radiation therapy; and for therapeutic targeting in BE patients with high-grade dysplasia or cancer, thereby offering a novel treatment approach for preventing disease recurrence or metastatic spread.

In addition to the potential diagnostic, prognostic and therapeutic utility of these lincRNAs, the molecular approaches outlined above can aid in curtailing the overall healthcare costs in this disease.

FIG. 1 shows a novel lincRNAs associated with EAC progression. Custom qPCR primers were designed to assess the relative expression levels of respective lincRNAs among the different lesions. Each dot represents a simple within the lesion-group. "EAC-cl" indicates the 5 EAC cell lines. Y-axis shows the fold-change in lincRNA expression value relative to the lowest expressing EAC (for Onco-linc's) and relative to the lowest expressing BE sample (for Suppressor-lincTMEM). ACTB (b-actin) was used an endogenous background control. The 4 "Onco-lincs" showed significant overexpression exclusively in EAC tissues (P<0.001) while lincTMEM showed significant down-regulation in EACs (P<0.001) as compared to non-malignant BE lesions. Overexpression of each of the Onco-lincs is also evident in the EAC cell lines, suggesting that these deregulations are localized within the tumor epithelia.

Figure 2:
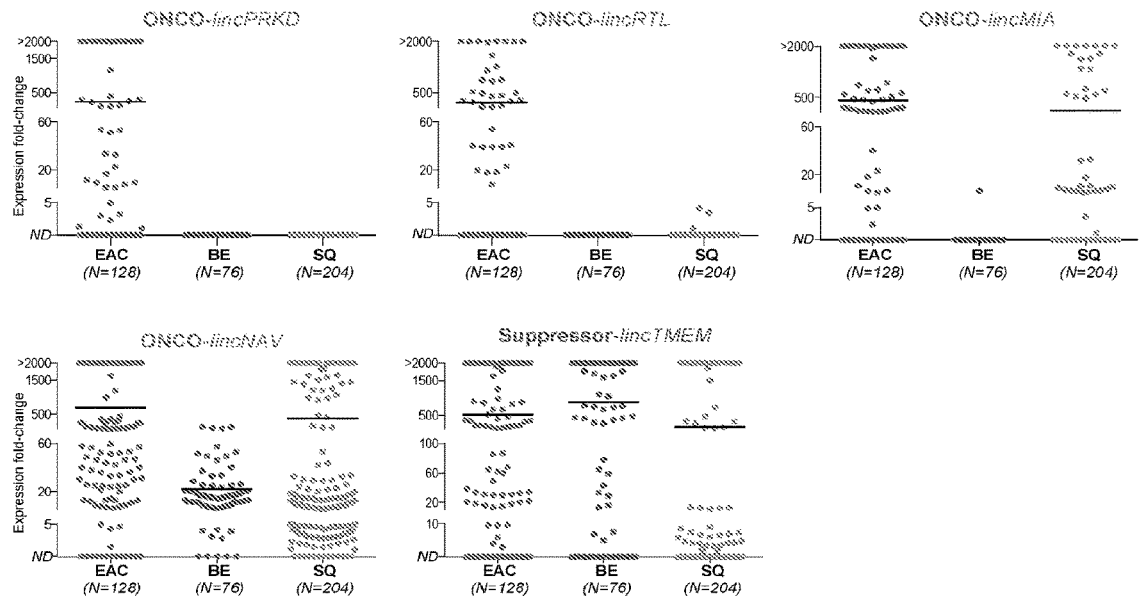
FIG. 2 illustrates plots showing validation of candidate lincRNAs in an independent cohort.

FIG. 2 shows validation of candidate lincRNAs in an independent cohort. qPCR analyses of candidate lincRNA in a large independent set of endoscopic biopsies. Each dot represents a simple within the lesion-group. "ND" on the Y-axis indicates expression not detected for the respective lincRNAs in respective samples. ACTB (b-actin) was used an endogenous background control. The 4 "Onco-lincs" showed significant overexpression in EAC tissues (P<0.001) as compared to the BE samples, while lincTMEM exhibited significant down-regulation in EACs (P<0.001) as compared to non-malignant BE lesions, thus confirming our findings in the discovery sample-set from FIG. 1.

Figure 3:
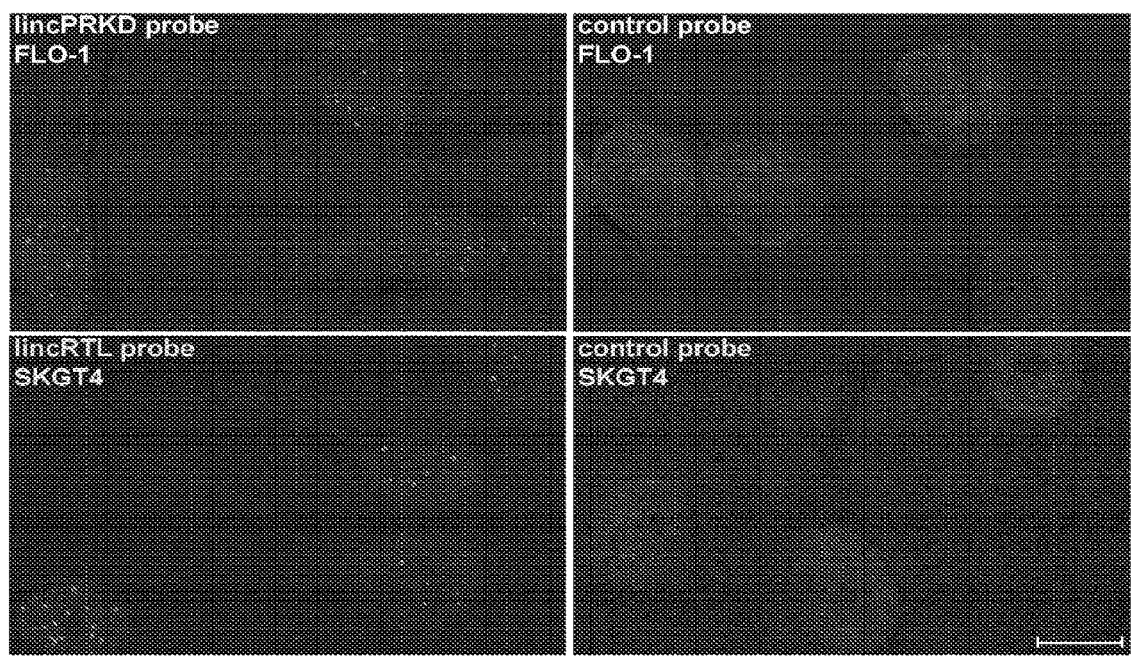
FIG. 3 illustrates RNAscope-based analysis of lincRNA sub-cellular localization.
Figure 4:
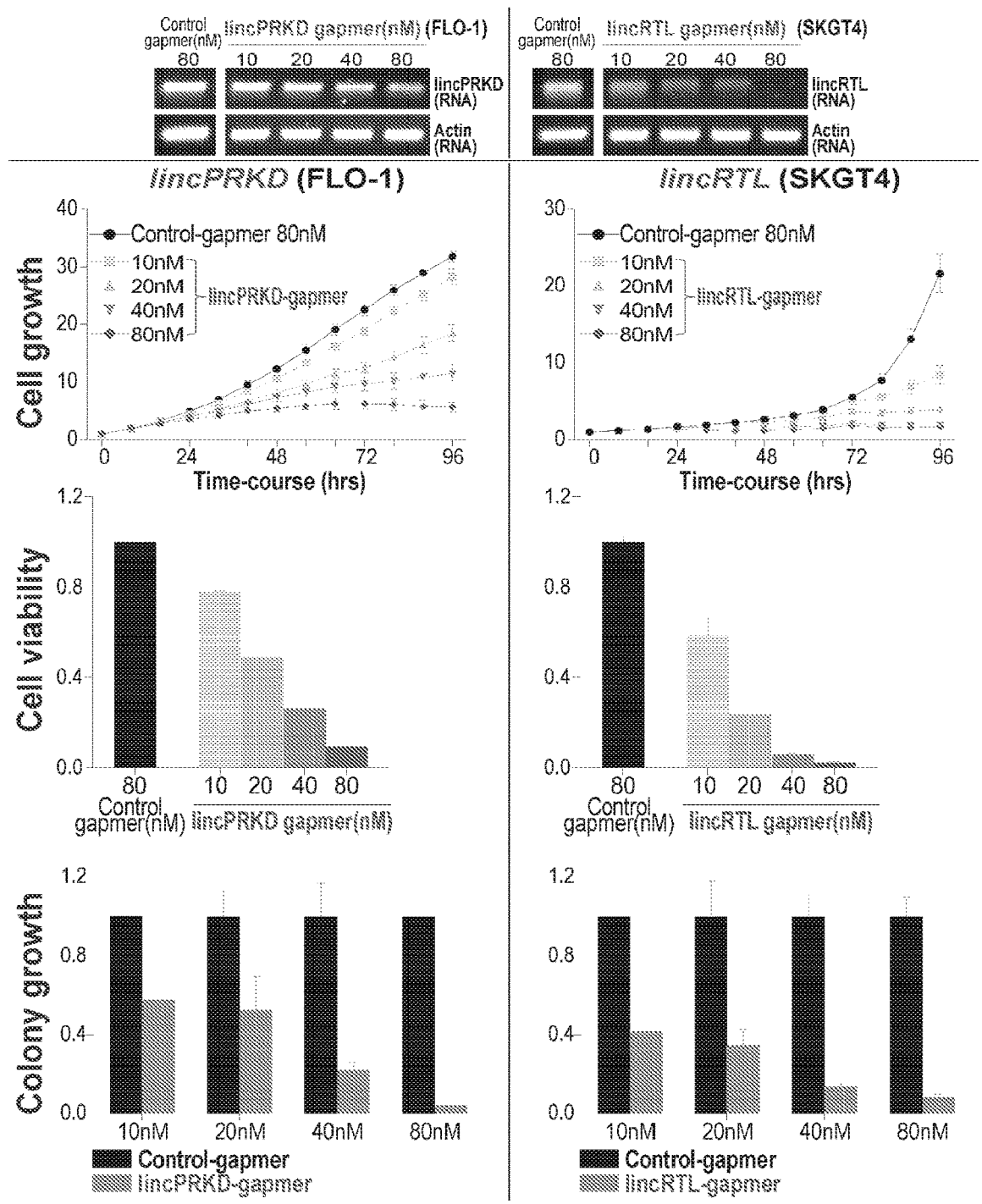
FIG. 4 illustrates immunoassays, plots, and graphs showing knock-down of Onco-lincPRKD and Onco-lincRTL leads to marked growth arrest of esophageal adenocarcinoma cells.

FIG. 3 shows RNAscope-based analysis of lincRNA sub-cellular localization. To assess the subcellular localization of candidate lincRNAs (Onco-lincPRKD, Onco-lincRTL), we designed custom RNAscope in situ probes against respective lincRNAs from Advanced Cell Diagnostics Inc (ACD). The resulting custom probe targeting lincRNA-PRKD was used on FLO-1 cells, and the custom probe targeting lincRNA-RTL was used on SKGT-4 cells. The experimental design included a negative control probe for each cell line. Images were captured using a Leica SP8 gSTED Super-Resolution Confocal set up to detect the fluorophore Atto 550, in conjunction with the Leica LAS X imaging software. Note that both Onco-lincPRKD and Onco-lincRTL show localization to the nucleus (red dots), suggesting that these Onco-lincRNAs may be involved in transcriptional regulation of other genes. DAPI was used as counter stain for the nucleus (blue color). This RNAscope system can be expanded to include FFPE, fresh frozen tissue, or fixed frozen tissue.

Knock-down of Onco-lincPRKD and Onco-lincRTL leads to marked growth arrest of esophageal adenocarcinoma cells. (Top panels) Flo-1 (left) and SKGT4 (right) cells were treated with gapmer antisense oligonucleotides (Exiqon) targeting lincPRKD and lincRTL, respectively, at varying concentrations or with control gapmer (80 nM). Total RNA isolated from the cells was subjected to PCR amplification of respective lincRNA transcripts, and PCR products were resolved on an agarose gel. Note the dose-dependent reduction of lincRNAs in cells treated with respective lincRNA-targeting gapmers, as compared to control gapmer treated cells. (Bottom panels) (Cell growth) Cells were plated in 96-well plates, and treated with either control gapmer (80 nM) or with varying concentrations of lincRNA-targeting gapmers. Growth measurements are expressed as percent cell confluence (Y-axis) normalized to time zero (X-axis) over a course of 96 hours following seeding, using the automated IncuCyte live-cell kinetic imaging system (Essen Bioscience). (Cell viability) Cells were treated as above for 96 hours, following which cell viability was assessed using CellTiter-Glo Luminescent Cell Viability Assay (Promega). Y-axis represents the fraction of live cells in each treatment group normalized to the control gamper (80 nM) treated cells. (Colony growth) Cells were seeded in 6-well plates and treated with varying concentrations of control or lincRNAtargeting gapmers. 8 days following treatment, colonies were counted and quantified using Alpha imager (Alpha Innotech). Y-axis represents fraction colony counts in each treatment group as compared to control-gapmer treated cells. All error bars represent Mean±s.e.m of 3 independent replicates per treatment group. Note that knock-down of lincPRKD or lincRTL in leads to marked dose-dependent suppression of cancer cell growth, cell viability, and colony growth, suggesting their potential implications as novel therapeutic targets in esophageal adenocarcinoma disease.

Following is the disclosure of chemical matter in the form of lincRNAs with the sequences and genomic locations (hg 19) of these four lincRNA transcripts along with their isoforms.

LincRNA transcript sequences:

lincRTL
linc-RTL chr14:101930489101938056 (SEQ ID NO: 1)
CATGCATTTTATTTGGCAAGTCTCTCTCACATCTTTAATCACACTAGC
CTGCCCACTGCCAATCAATAAAGATTAGGAAATCGATTGCTAACTTACTC
TTGGGTTAGATAATAAAATTGTTTGAAACATGCACCTGGAGGAATTTATC
TGTGAAGAGTCCTTTCAGAGTTTGTTTCAAGCTTTGCAAGTCTCTCATGG
CTCTGAGGTCGGGGAGGCTGTGAGGGATCCTCCACGCCCAGCAGACGTGG
AAGGAGCCGACGTTCTTACGGGAGATGGACAGACGGTCAGCATGTGAATA
GTCCCCTGCATGCAGGTGAGGACTGGGGCAGTGCAGAGCCGCAGCAGGGA
TGGGCTATGCCTGGGAGCCGCCAGCTCTGGATCAGGTGGCCAGGGACGGT
CATGCTGAAGAGGAAGGCTCCAGTGAAGCTCTGGAAGAATGTTCTGGTGC
AGAGAGGGGGTGGGTGAGCTGGTTCCCATGGAGACAGGCTCAGGATCCCC
AGAGGCCACCAGTCCTTTCTTCGTCTGACGGGAGGGAGGGCCTTCCGACA
AGTCACGGAACTGATCGGGGAGAGCTGGATGCCTGCTACACCGTGGCTC
TGCTGTCTCCCGTGAAACCCGGGCCTCTGTTCGAGCCTGAAGTGGCCTC
TCTGCACCAGGCTGCTGGGAGACCTGCAGTCACCAATGGCAACGTCACTC
TTGCAACAGCCAGTGGGGTGTGGGGCAGCAGACGAAGCTCGAGTACCGCG
TTCTTCCATGTCCAGCATTCTGCTTTCAGCATCACGGGAACGAGAGGTGA
TTTCCGTAAGCAGGCTCCAAGGTGCCACCACCAAGCCCAGAAGTATCTTT
CCCACTTTGCAGATTTCCTACAGACCCAGTATTCTCTCTTCCATGGGTTG
AGTTTCTAAAATCACATGACTGTATTTTTCTTTTAATACAGAAAAGCATA
ATAAAGGCATAAAAGCCCATGCCCCTCTGCAGAGCACCCTGTTGACATTT
TCTGAAAGTAAGTCATCTATGCACCTGGGAAGAAAGCACAGAGGACTCAG
AAAGGCCAAAAACAAAAACAAAAAAGCCCCACCTCAGCCCCTGCCCCTCT
CCCGGAGAAGCCGGAGTTGTCAGCCCATGCAGCAGAGTTGGTCAGGAGCT
CAAGTTCACATCCCCAACCGCCACATACTACCTGTATCACCTGGGCAGG
TTCTCCCAATACCTCAGTGTCTTCATCTGCAACGTGGGTAAGATGGGAAT
GCCCACCTCCTGGGGAACTCAGGACTCGCTGAGTTAACTGCATTCAGGGA
CCTGAAAGAGACTCGCCAGGCAGTAACCCCAGTCCACTTGTTCCATGCTG
GTGTGAGCAGTGACTGCATATTCTTCCAAAAGCATCTACCCCATCTATTT
TTTTTTTTTTTTTTGAGACAGGGTCTCCCTCTGTCACCCAGGCTGGAGT
GCAGTGGCATGATCTCAGCTCACTGCAACCTCCACCTCCCGGGTTCAAGC
GATTCTCCCGCCTCAGCCTCCTGAGTAGCTGGGATTACAGGCGTGCACCA
CCATGCCCAGCTAATTTTTGTATTTTTAGTAAAGACAGGGTTTCACCATA
TTGCTCAGGCTGGTCTGGAACTCCCAACCTCAGGTGATCTGCCCACCTCA
GCCTCTCCAAGGTGCTGGGATTACAGGCGTGAGCCACCGCGCTGCCTATAC
TATCTATTTGTTAAGCCCCAAATGGATCATACTTTGGTTCAGCCTCTTGC
GTTCTTTGCCTTGTTTATTTTAGAGACTGTCTATCTCAATCCATGCAGA
TAAATGCCTTGCTCTTTCTTAGGTGCCACCAAGCATAGACACAGACCTCC
CCAATGCCCCATCTTTCGCCATTAATCAACAGTGTTGGGATGGTAGGACA
CCAGGAGTTAGACACCTCAAAGCACCGGTTCTG.

lincMIA
linc-MIA isoform 1 chr1:222139610-222141838
(SEQ ID NO: 2)
CTCAGCCCACCTGCACCCAGGTGAAATAAACAGCCATGTTGCTCACA
CAAAGCCTGTTTGGTGGTCTCTTCACACAGATGTGCATGAAATTTGGTGT
GGTGACTCGGATCGGGGGACCTGCCTCAGGAAATCAATCCCCTGTCCTCC
TGCTCTTTGCTCCGTGAGAAAGATCCACCTACGACCTCAGGTCCTCAGAC
CGACTAGCCCAAGAAACATCTCACCAATTTCAAATCTGCACTCCCAGAGC
CCGTGGAACTCTGGCCCAAGGCTCTCTGACTGACTCCTTCTTGGCTTAGC
GGCTGAAGACTGACACTGCCCGATCGCCTCAGAAACCCCGTAGACCATCA
CGGACGCCGAGCTTTAGTTAACTCTCACAGTGGAGG.

linc-MIA isoform 2 chr1:222139610-222156485
(SEQ ID NO: 3)
CTCAGCCCACCTGCACCCAGGTGAAATAAACAGCCATGTTGCTCACA
CAAAGCCTGTTTGGTGGTCTCTTCACACAGATGTGCATGAAATTTGGTGT
GGTGACTCGGATCGGGGGACCTGCCTCAGGAAATCAATCCCCTGTCCTCC
TGCTCTTTGCTCCGTGAGAAAGATCCACCTACGACCTCAGGTCCTCAGAC
CGACTAGCCCAAGAAACATCTCACCAATTTCAAATCTGCACTCCCAGAGC
CCGTGGAACTCTGGCCCAAGGCTCTCTGACTGACTCCTTCTTGGCTTAGC
GGCTGAAGACTGACACTGCCCGATCGCCTCAGAAACCCCGTAGACCATCA
CGGACGCCGAGCTTTAGTTAACTCTCACAGTGGAGGCCTTTGCAAGAGGG
TCCGAGACATTTGCATCATCATTCAGTGAGACCTGTAAACACAGCATCTG
CCTTTGACCACATCCATCTGGAAGAACCTGAGAGATAATCCATTTTATGA
AATTTTCCCTACCCTGAAATGGGAGAATG.

linc-MIA isoform 3 chr1:222139610-222156485
(SEQ ID NO: 4)
CTCAGCCCACCTGCACCCAGGTGAAATAAACAGCCATGTTGCTCACA
CAAAGCCTGTTTGGTGGTCTCTTCACACAGATGTGCATGAAATTTGGTGT
GGTGACTCGGATCGGGGGACCTGCCTCAGGAAATCAATCCCCTGTCCTCC
TGCTCTTTGCTCCGTGAGAAAGATCCACCTACGACCTCAGGTCCTCAGAC
CGACTAGCCCAAGAAACATCTCACCAATTTCAAATCTGCACTTTGCAAGAG
GGTCCGAGACATTTGCATCATCATTCAGTGAGACCTGTAAACACAGCATC
TGCCTTTGACCACATCCATCTGGAAGAACCTGAGAGATAATCCATTTTAT
GAAATTTTCCCTACCCTGAAATGGGAGAATG.

linc-MIA isoform 4 chr1:222139610-222159240
(SEQ ID NO: 5)
CTCAGCCCACCTGCACCCAGGTGAAATAAACAGCCATGTTGCTCACA
CAAAGCCTGTTTGGTGGTCTCTTCACACAGATGTGCATGAAATTTGGTGT
GGTGACTCGGATCGGGGGACCTGCCTCAGGAAATCAATCCCCTGTCCTCC
TGCTCTTTGCTCCGTGAGAAAGATCCACCTACGACCTCAGGTCCTCAGAC
CGACTAGCCCAAGAAACATCTCACCAATTTCAAATCTGCACTCCCAGAGC
CCGTGGAACTCTGGCCCAAGGCTCTCTGACTGACTCCTTCTTGGCTTAGC
GGCTGAAGACTGACACTGCCCGATCGCCTCAGAAACCCCGTAGACCATCA
CGGACGCCGAGCTTTAGTTAACTCTCACAGTGGAGGCCTTTGCAAGAGGG
TCCGAGACATTTGCATCATCATTCAGTGAGACCTGTAAACACAGCATCTG
CCTTTGACCACATCCATCTGGAAGAACCTGAGAGATAATCCATTTTATGA
AATTTTCCCTACCCTGAAATGGGAGAATGATCTAATTTGAAGCACTGAGA
AGGATAAGGCATCCATTTGAAAAGGACTCCTATATTGCAACATGAATTCT
GCTAAAATTGAAGCAAGAACAAACATCAAATTTATGATGAAGTTTGGGTA
GAAGAACGATGAAATTAGTGACGCTTTATAAAAAGTTTATTGGGACAATA
CCCCAAATGAATCAGCAGTTTAAAAATGGATAACTTATTTTAAGAAGAAA
CAAGATGATGTTGAAGATGAAGCCTGCAACGGCAGACCATCTACATCAAT
TTGGAAGGAAAAAATTAATCTTGTTCATGCCCTAACGGAGGAAGACTGAC
AATTAACAGCACTGACAATAGCCAACAATGTAGACAGCTGGTTCACCTTA
CACAATTCTGAGTGAAAAATTAAAATTGAGCAAACTTTCCACTCAATGAG
TACCAAAACTGTTGTACCCAGGTTAGCTGCAAATAACAGCAGAACTTTCA
ATTGAAATTTTAAACAAGTGGGATCAAGATCCTGTAGCATTTCCTTGAAG
AACTGTAACAGGAGATGAAACATGACTTTACAATATGATCCCAAAGACAT
AATCAAAGCATAATCAAAGCAATGCTGCCAAGAGGTGGAAATGGTCAAG
TCACAGCAAAAGCAGATGAGCAATGAGCAAAGGTCATGGCAAAGTTTTTT
GGTGATGTTCAAGGTGTTTTACTCGTTGACTTTCTGGAGGGCCAAAAAAC
AATAACATCTACTAATTATGAGAGTATTTTGAGAAAGTCCGTCAAAGTTT
TAGCAGAAAAACACCCAGGAAAGTTTCACCAGAGAGTCCTTCTTCACCAT
GACAATGTTCCTACTCATTTTTCTCATCAAACAAGGGCAATTCTGTGAGA
TTTTCCATGAGAAATCATTAGGCATCCACCTTACAGTCCTGGTTTGGTTC
CTTCTAACTTCTTTTGTTTCCTAATCTTAAGAAACTTTTTACCTTAAGT
TAAAGTATATAGCTATTTAAGATTTCCTAATCTTAAAAAAATTTTTCTTC
AGTTGATAATATGAAAAGATTGCACTGACATAGTTAAATTCCCAAGACC
CTCAGTTCTTTATGAATGAACCAAATGGCTGATGTCATTGTTTATAAAAG
TGACTTGAACTTAACGTTCTGGTAAACCAGCACCAGCCTGAAGATCACGT
TCTCATCAAACGGTGGAAAGAAGAAAAACTCGAGCCAACCTAGGAAGGAC
CCCACCTTGTGCTGCTAACCACCAAG lincPRKD
linc-PRKD isoform 1 chr14:30907276-30943473
(SEQ ID NO: 6)
CTGAATCTTCCATAAGTACTTTAGAATTCAGAGAAAGAAGGAATCTA
TGAGCCCGAATCTCCAGGGAAGGCCTCGAGGAGTGGTCATGGTTTAACCT
TAGTTCCAGCTTCGGAAATGAGGAGGTAGGGAAAGAAGCAGCAAAAATTC
TCAGCCAGACTTTGAACAGGAAGCTTTAGTAAGAGACGTGAATATCTTTT
AAAAATAAAAGAAGGTTGACACAGAGATCCAGGAGCCAAGATGGCCGAAT
AGGAACAGCTCCGGTCTACAGCTCCCAGCGTGAGCCACGCAGAAGACGGG
TGATTTCTGCATTTCCATCTGAGGTACCGGGTTCATCTCACTAGGGAGTG
CCACACATGGGCGCAGGTCAGTGGGTGCGTGCACCGTGCGCGAGCCGAA
GCAGGGCGAGGCATTGCCTCACTCCGGAAGCGCAAGGGGTCAGGGAGTTC
CCT.

linc-PRKD isoform 2 chr14:30938467-30943473
(SEQ ID NO: 7)
AGGTGTTTCCAGAAGAGGTGAGCAATTGAATCAGCAAACTAAACAA
AGATTGTCCTCATCAATGTAGGTGAGCATCAGCTAACCCAGGAAGGGCTT
TAATCTCTGCTGTGGCCAGTTTCTATTTCAGCCTTATAATTTTCTGCATT
TCCTTCCTCTATTGCTTTTCATCCACACTTTATTTAGGAAATGTTCAACA
GAGAAGCCAGAAAGGTACCTCTTCGGAAATGAGGAGGTAGGGAAAGAAGC
AGCAAAAATTCTCAGCCAGACTTTGAACAGGAAGCTTTAGTAAGAGACGT
GAATATCTTTTAAAAATAAAAGAAGGTTGACACAGAGATCCAGGAGCCA
GATGGCCGAATAGGAACAGCTCCGGTCTACAGCTCCCAGCGTGAGCCACG
CAGAAGACGGGTGATTTCTGCATTTCCATCTGAGGTACCGGGTTCATCTC
ACTAGGGAGTGCCACACATGTGGGCGCAGGTCAGTGGGTGCGTGCACCGTG
CGCGAGCCGAAGCAGGGCGAGGCATTGCCTCACTCCGGAAGCGCAAGGGG
TCAGGGAGTTCCCT.

linc-PRKD isoform 3 chr14:30938467-30961930
(SEQ ID NO: 8)
AGGTGTTTCCAGAAGAGGTGAGCAATTGAATCAGCAAACTAAACAA
AGATTGTCCTCATCAATGTAGGTGAGCATCAGCTAACCCAGGAAGGGCTT
TAATCTCTGCTGTGGCCAGTTTCTATTTCAGCCTTATAATTTTCTGCATT
TCCTTCCTCTATTGCTTTTCATCCACACTTTATTTAGGAAATGTTCAACA
GAGAAGCCAGAAAGGTACCTCTTCGGAAATGAGGAGGTAGGGAAAGAAGC
AGCAAAAATTCTCAGCCAGACTTTGAACAGGAAGCTTTAGTAAGAGACCC
TGTAA.

LincRNA transcript sequences:

linc-PRKD isoform 4 chr14:30907276-31029946
(SEQ ID NO: 9)
CTGAATCTTCCATAAGTACTTTAGAATTCAGAGAAAGAAGGAATCTA
TGAGCCCGAATCTCCAGGGAAGGCCTCGAGGAGTGGTCATGGTTTAACCT
TAGTTTTG.

linc-PRKD isoform 5 chr14:30921167-30943473
(SEQ ID NO: 10)
CCAGCTTCGGAAATGAGGAGGTAGGGAAAGAAGCAGCAAAAATTCT
CAGCCAGACTTTGAACAGGAAGCTTTAGTAAGAGACGTGAATATCTTTTA
AAAATAAAAGAAGGTTGACACAGAGATCCAGGAGCCAAGATGGCCGAATA
GGAACAGCTCCGGTCTACAGCTCCCAGCGTGAGCCACGCAGAAGACGGGT
GATTTCTGCATTTCCATCTGAGGTACCGGGTTCATCTCACTAGGGAGTGC
CACACAGTGGGCGCAGGTCAGTGGGTGCGTGCACCGTGCGCGAGCCGAAG
CAGGGCGAGGCATTGCCTCACTCCGGAAGCGCAAGGGGTCAGGGAGTTCC
CT.

lincTMEM
linc-TMEM isoform 1 chr12:126515202-126527981
(SEQ ID NO: 11)
CCAGGCAGTCACCTAGCTGCTGTTATGCTGCATACCTGTCTCTGAGTA
CTCGCTTCATCCATCGGCCAGGGTCTGTGGGACAGACCAGGCAGGTGGTG
CCCCATGTGAGGAACGCTGCAATGGATTGCAAGGGAACCCCTGAAAACAA
ATGTGAAGTGACTGAGCATGTTAACCTTAGAAGACTAGAACCTAATGAGT
TATGGCAAACAGATGTTATGCACGTCCCTGAATTTGGAAAACTAAGACGA
GGCATCAAACCATACCATGGCATGGCTAGGACCCAACCCGGTACCAAAAT
GAAGAAATGACCCTACAGGACCCACAATCCCGGATGATGTGGCTTCCTT
GGATGACACAGGCCCTGGACATTACCTGGGGGATGCTGAAGAAGACAACT
CAGGAGGCCAAGCAAATCCTGCTCCAGGCACAGACACCATTCACTCCAGA
AGCTGCCATTCATTCGACATAAGTAGGTGCTTCATCTGATAAGCGCTGCT TGTGTAATTTATCAATGACAGAGAAGGCAGATAGCAGCATGCATACTTGG
GGCTGCATTTGAAGGAGAGCAACATCCCTTTGTTTTCACAGAGAGAACAA
GCATGAGTTGAGATTGTGGTGCTTCTTGAAGTCTCATCCAGATCAGAAAC
CTGCTGCTCTGTCCACATTCCATCCACCAAAGCAACCCATATGGCCATGT
CCAGCATCAGATGGGGAAAGGCAGTTCTCCTCTAGCACGAGGAGCTGCAA
AGCCACATGGCAAAGGATGAGTG.

linc-TMEM isoform 2 chr12:126515202-126535829
(SEQ ID NO: 12)
CCAGGCAGTCACCTAGCTGCTGTTATGCTGCATACCTGTCTCTGAGTA
CTCGCTTCATCCATCGGCCAGGGTCTGTGGGACAGGCAGGTGGTG
CCCCATGTGAGGAACGCTGCAATGGATTGCAAGGGAACCCCTGAAAACAA
ATGTGAAGTGACTGAGCATGTTAACCTTAGAAGACTAGAACCTAATGAGT
TATGGCAAACAGATGTTATGCACGTCCCTGAATTTGGAAAACTAAGGTCC
TCTTTGGATTCCAGCACGAGGCATCAAACCATACCATGGCATGGCTAGGA
CCCAACCCGGTACCAAAATGAAGAAAATGACCCTACAGGACCCACAATCC
CGGATGATGTGGCTTCCTTGGATGACACAGGCCCTGGACATTACCTGGGG
GATGCTGAAGAAGACAACTCAGGAGGCCAAGCAAATCCTGCTCCAGGCAC
AGACACCATTCACTCCAGAACTCCAGAAGAGAAGGGCCTTTTTCCACTGT
GTCCATTGATGAATCTTCATCACTGAGAATGGAATATGCCACATAGCAGA
TGCTCAATAAATATGTTGA.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, we claim:

1. A method of monitoring the progression of cancer and treatment of cancer in a subject,
   obtaining an expression profile from a sample of tissue obtained from the subject, wherein the expression profile comprises the level of at least one esophageal adenocarcinoma associated lincRNA selected from the group consisting of linc-PRKD, lincRTL, lincMIA, lincNAV, and lincTMEM, and
   comparing the expression profile from the sample to an expression profile of a control or standard, wherein a decrease in the expression of the at least one esophageal adenocarcinoma associated lincRNA selected from lincTMEM and/or an increase in the expression of the at least one esophageal adenocarcinoma associated lincRNA selected from the group consisting of lincPRKD, lincRTL, lincMIA, and lincNAV is indicative of the subject having cancer or an increased risk of cancer; and
   administering to the subject with decreased expression of lincTMEM or increased expression of at least one of lincPRKD, lincRTL, lincMIA, and lincNAV an agent that is effective to modulate the level esophageal adenocarcinoma associated lincRNA in the esophageal cells or esophageal cancer cells.

2. The method of claim 1, wherein the expression profile of the control or standard is an expression profile from a healthy subject or a subject with Barrett's esophagus and not esophageal cancer.

3. The method of claim 1, wherein the sample of tissue is a gastric biopsy cell or tissue sample.

4. The method of claim 1, wherein an increase in the expression of the at least one esophageal adenocarcinoma associated lincRNA is indicative of the subject having high grade dysplasia and/or esophageal cancer or an increased risk of high grade dysplasia and/or esophageal cancer.

5. The method of claim 4, wherein the lincRNA is lincPRKD or lincRTL.

6. The method of claim 1, wherein a decrease in the expression of the at least one esophageal adenocarcinoma associated lincRNA is indicative of the subject having high grade dysplasia and/or esophageal cancer or an increased risk of high grade dysplasia and/or esophageal cancer.

7. The method of claim 6, wherein the lincRNA is lincTMEM.

8. The method of claim 1, wherein the subject has or is suspected of having Barrett's esophagus and/or gastroesophageal reflux disease.

9. A method of treating and monitoring a subject's response to a treatment regimen for cancer; the method comprising:
   administering a therapeutic regiment to the subject;
   obtaining an expression profile from a sample of cancer cells obtained from the subject, wherein the expression profile comprises the level of at least one esophageal adenocarcinoma associated lincRNA selected from the group consisting of linc-PRKD, lincRTL, lincMIA, lincNAV, and lincTMEM,
   comparing the expression profile from the sample to an expression profile of a control or standard, wherein an increase in the expression of the at least one esophageal adenocarcinoma associated lincRNA selected from lincTMEM and/or a decrease in the expression of the at least one esophageal adenocarcinoma associated lincRNA selected from the group consisting of lincPRKD, lincRTL, lincMIA, and lincNAV is indicative of an increased efficacy of the therapeutic regimen.

10. The method of claim 9, wherein the expression profile of the control or standard is an expression profile of at least one esophageal adenocarcinoma associated lincRNA selected from the group consisting of linc-PRKD, lincRTL, lincMIA, lincNAV, and lincTMEM of cancer cells obtained from the subject prior to administration of the therapeutic regimen.

11. The method of claim 9, wherein the sample of tissue is a gastric biopsy cell or tissue sample.

12. The method of claim 9, wherein a decrease in the expression of the at least one esophageal adenocarcinoma associated lincRNA is indicative of increased efficacy of the therapeutic regimen in treating high grade dysplasia and/or esophageal cancer.

13. The method of claim 12, wherein the lincRNA is lincPRKD or lincRTL.

14. The method of claim 9, wherein an increase in the expression of the at least one esophageal adenocarcinoma associated lincRNA is indicative of increased efficacy of the therapeutic regimen in treating high grade dysplasia and/or esophageal cancer.

15. The method of claim 14, wherein the lincRNA is lincTMEM.

16. The method of claim 9, wherein the subject has or is suspected of having Barrett's esophagus and/or gastroesophageal reflux disease.

17. The method of claim 9, wherein the therapeutic regimen comprises at least one of radiation therapy or chemotherapy.

* * * * *